(12) United States Patent
Thornton

(10) Patent No.: US 11,589,991 B2
(45) Date of Patent: Feb. 28, 2023

(54) DELIVERY SYSTEM FOR MITRAL VALVE LEAFLET APPOSITION DEVICE

(71) Applicant: Troy Thornton, San Francisco, CA (US)

(72) Inventor: Troy Thornton, San Francisco, CA (US)

(73) Assignee: Troy Thornton, San Francisco, CA (US)

( * ) Notice: Subject to any disclaimer, the term of this patent is extended or adjusted under 35 U.S.C. 154(b) by 231 days.

(21) Appl. No.: 16/615,844

(22) PCT Filed: Jun. 21, 2018

(86) PCT No.: PCT/US2018/038792
§ 371 (c)(1),
(2) Date: Nov. 22, 2019

(87) PCT Pub. No.: WO2018/237165
PCT Pub. Date: Dec. 27, 2018

(65) Prior Publication Data
US 2020/0138578 A1     May 7, 2020

Related U.S. Application Data

(60) Provisional application No. 62/552,951, filed on Aug. 31, 2017, provisional application No. 62/523,193, filed on Jun. 21, 2017.

(51) Int. Cl.
*A61F 2/24* (2006.01)
*A61M 25/01* (2006.01)
*A61M 25/00* (2006.01)

(52) U.S. Cl.
CPC .......... *A61F 2/2466* (2013.01); *A61F 2/2442* (2013.01); *A61F 2210/0014* (2013.01); *A61M 25/0133* (2013.01); *A61M 2025/0025* (2013.01)

(58) Field of Classification Search
CPC .................. A61F 2/2466; A61F 2/2442; A61F 2210/0014; A61M 25/0133
See application file for complete search history.

(56) References Cited

U.S. PATENT DOCUMENTS

| | | |
|---|---|---|
| 5,411,025 A | 5/1995 | Webster |
| 6,269,819 B1 | 8/2001 | Oz et al. |
| 6,461,366 B1 | 10/2002 | Seguin |
| 6,629,534 B1 | 10/2003 | St. Goar et al. |
| 6,752,813 B2 | 6/2004 | Goldfarb et al. |

(Continued)

*Primary Examiner* — William H Matthews
(74) *Attorney, Agent, or Firm* — Shay Glenn LLP

(57) ABSTRACT

A delivery system for an interventional device includes an elongate catheter body, a catheter shaft extending within the elongate catheter body and configured to releasably attach to the interventional device, and at least one flexible element attached to a distal portion of the catheter shaft. The at least one flexible element has an expanded configuration in which the at least one flexible element extends beyond an outer circumference of the elongate catheter body and a collapsed configuration in which the at least one flexible element collapses within an inner circumference of the elongate catheter body. The at least one flexible element is configured to act as a tactile stop when pulled proximally against the elongate catheter body and/or to fold over the interventional device to act as a retraction aid.

16 Claims, 22 Drawing Sheets

(56) References Cited

U.S. PATENT DOCUMENTS

| | | |
|---|---|---|
| 7,048,754 B2 | 5/2006 | Martin et al. |
| 7,226,467 B2 | 6/2007 | Lucatero et al. |
| 7,563,267 B2 | 7/2009 | Goldfarb et al. |
| 7,604,646 B2 | 10/2009 | Goldfarb et al. |
| 7,666,204 B2 | 2/2010 | Thornton et al. |
| 8,216,256 B2 | 7/2012 | Raschdorf et al. |
| 2003/0036698 A1 | 2/2003 | Kohler et al. |
| 2005/0288551 A1 | 12/2005 | Callister et al. |
| 2009/0171434 A1 | 7/2009 | Rusk et al. |
| 2012/0053680 A1* | 3/2012 | Bolling ............... A61F 2/2466 623/2.11 |
| 2014/0128844 A1 | 5/2014 | Kornowski et al. |
| 2016/0022290 A1* | 1/2016 | Johnson ............... A61B 8/12 606/159 |
| 2017/0165064 A1 | 6/2017 | Nyuli et al. |
| 2020/0222187 A1 | 7/2020 | Thornton et al. |

\* cited by examiner

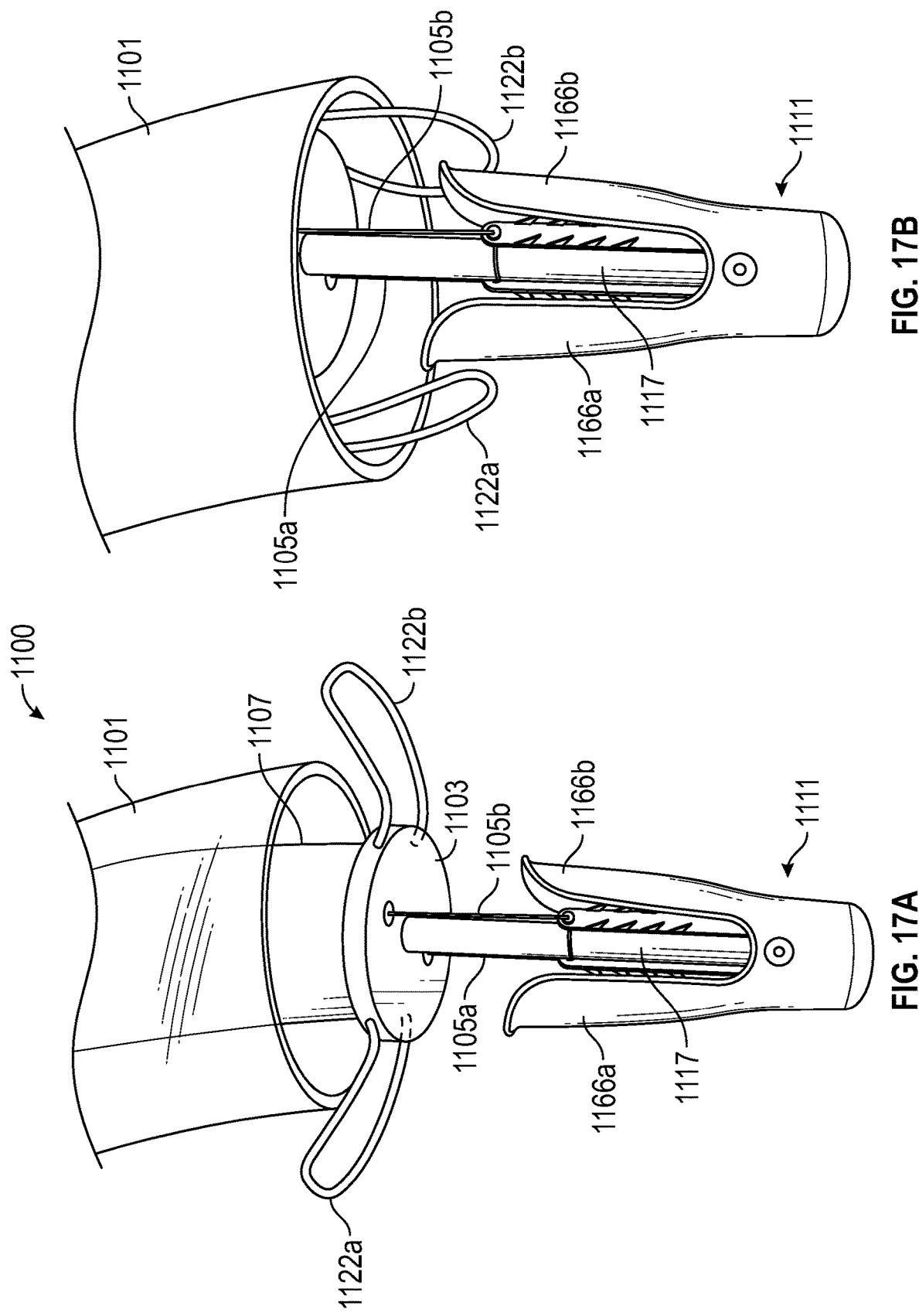

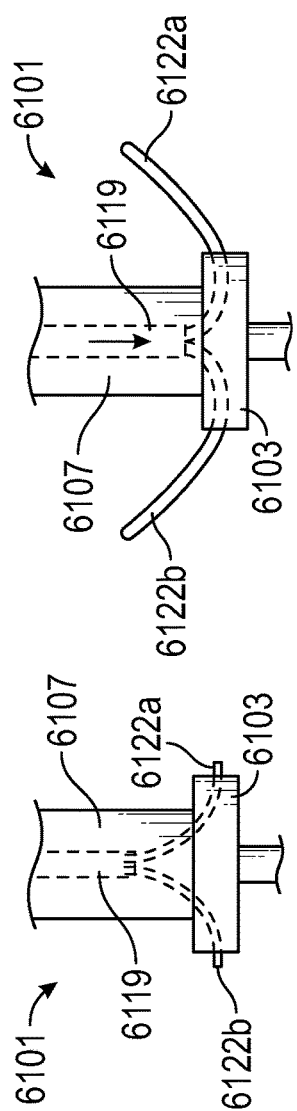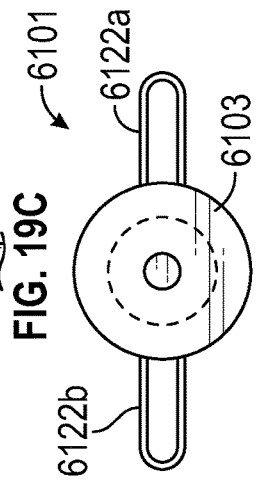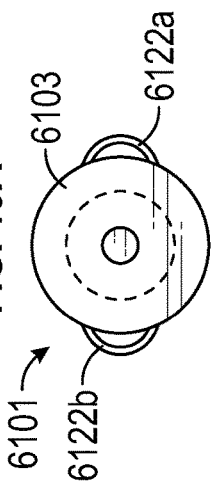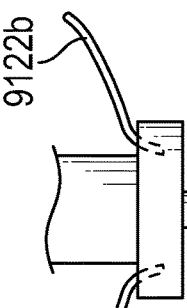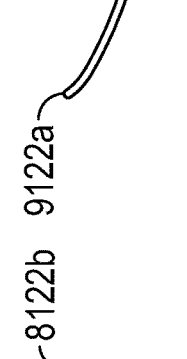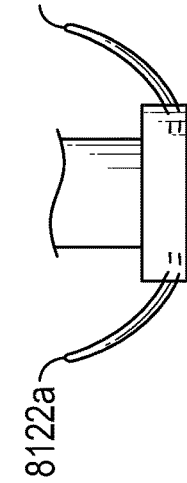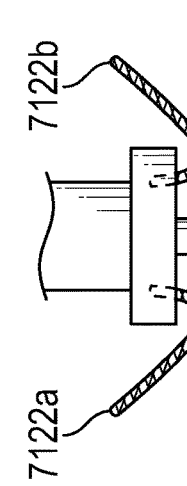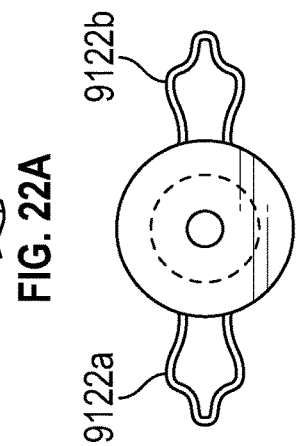

DELIVERY SYSTEM FOR MITRAL VALVE LEAFLET APPOSITION DEVICE

CROSS REFERENCE TO RELATED APPLICATIONS

This application claims priority to U.S. Provisional Patent Application No. 62/523,193, filed Jun. 21, 2017, and titled "SINGLE CATHETER STEERABLE DELIVERY SYSTEM FOR MITRAL VALVE LEAFLET APPOSITION DEVICE," and to U.S. Provisional Application No. 62/552,951, filed Aug. 31, 2017, and titled "DELIVERY SYSTEM FOR MITRAL VALVE LEAFLET APPOSITION DEVICE", the entireties of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

A variety of endovascular catheter-based interventional devices or tools have been developed to modify the mitral valve in order to treat mitral insufficiency. Many of these interventional devices require a steerable catheter delivery system in order to achieve the desired position and alignment over the mitral valve. Often, these delivery systems are inserted into the femoral vein and are then crossed through the interatrial septum to a position in the left atrium. The interventional device is then inserted into the catheter and positioned in such a way as to allow modification of the mitral valve. Various modifications are possible, whether it be through a leaflet apposition device, an annulus-modification device, a chordal shortening device, a regurgitation blocking device, or the like.

Referring to FIG. 1A, one exemplary leaflet apposition device, a mitral valve clip 99, includes two arms 66a,b that open to grasp the leaflets and then close to a smaller angle in order to bring the leaflets closer together to resolve mitral regurgitation. Barbed grippers 97 further hold the tissue in place once activated. During delivery, the arms 66a,b are closed to a tight angle in order to allow the clip 99 to fit within and be advanced through the guiding catheter 98, as shown in FIG. 1B.

During use of the mitral valve clip 99, there are instances in which the physician/user needs to retract the mitral clip back into the guiding catheter 98 and remove it from the patient. This can occur, for example, if the mitral clip 99 is unable to grasp the leaflets, if a different size of mitral clip 99 is desired, or if the mitral clip 99 malfunctions. To retract the clip 99, extra precautions can be taken to minimize the risk that one of the clip arms 66a,b catches on the outside of the guiding catheter 98. For example, the clip arms 66a,b can be closed very tightly, one or more curves in the guiding catheter 98 can be straightened, and the clip arms 66a,b can be rotated while looking under fluoroscopy. Even with these extra precautions, however, it is still possible for the clip 99 to get temporarily or permanently caught on the soft distal tip of the guiding catheter 98, as shown in FIG. 2. This can result in extra time and difficulty for the physician, polymer embolization (from the physician's maneuvers to try to release the clip), clip damage, patient injury, and/or surgery to remove the clip from the patient.

Further, for delivery of leaflet apposition devices, such as a mitral valve clip, a two-catheter steering and delivery system is often used because curving the catheter in two different planes is required. In these systems, the two catheters, one inside the other, are designed to curve in two different planes. The delivery catheter is required to be torquable and to advance and retract within the two steering catheters. Use of a two catheter steering and delivery system, however, can be difficult to use and expensive and can also limit the size of the device being delivered.

Single catheter steering and delivery systems, however, run the risk of getting portions of the interventional devices becoming stuck on the inner diameter of the catheter. For example, barbed grippers 97 of the mitral valve clip 99 might catch on the curved diameter of the guiding catheter 98, as shown in FIG. 3. If this happens, polymer can be released into the patient an/or removal of the mitral valve clip 99 from the single catheter steering and delivery system can be prevented, requiring removal of the whole system from the patient, possibly by open surgery.

A delivery system that addresses some or all of these problems is described herein.

SUMMARY OF THE DISCLOSURE

The present invention relates to a single catheter steerable delivery system that can be used, for example, to deliver a mitral valve leaflet apposition device.

In general, in one embodiment, a delivery system for an interventional device includes an elongate catheter body, a catheter shaft extending within the catheter body and configured to releasably attach to the interventional device, and at least one flexible element attached to a distal portion of the catheter shaft. The at least one flexible element has an expanded configuration in which the at least one flexible element extends beyond an outer circumference of the elongate catheter body and a collapsed configuration in which the at least one flexible element collapses within an inner circumference of the elongate catheter body. The at least one flexible element in the expanded configuration is configured to provide a tactile stop when moved proximally relative to and against a distal end of the elongate catheter body with a first amount of force. The at least one flexible element is configured to collapse from the expanded configuration to the collapsed configuration to fit within the elongate catheter body when the at least one flexible element is moved relative to and against the distal end of the elongate catheter body with a second amount of force that is greater than the first amount of force.

This and other embodiments can include one or more of the following features. The at least one flexible element can be configured to self-expand from the collapsed configuration to the expanded configuration when released from the elongate catheter body. The at least one flexible element can include two flexible elements, and the two flexible elements can be positioned opposite one another about the distal portion of the catheter shaft. The distal portion can include a cylindrical tip of the catheter shaft, and the cylindrical tip can have a larger diameter than a proximal portion of the catheter shaft. The at least one flexible element can be a looped element extending from the distal portion of the catheter shaft. The at least one flexible element can be a tab extending from the distal portion of the catheter shaft. The at least one flexible element can be an annular ring extending around the distal portion of the catheter shaft. The at least one flexible element can be a spring-activated ball bearing. The at least one flexible element can include a polymer. The at least one flexible element can include a shape memory alloy. The at least one flexible element can include stainless steel. The elongate catheter body can be a steerable elongate catheter body. The elongate catheter body can include a plurality of cables configured to be activated to steer the elongate catheter body. The elongate catheter body can be the only steerable elongate catheter body in the delivery system. The at least one flexible element can be attached to the distal portion of the catheter shaft at an attachment location, and the at least one flexible member in the collapsed configuration can have a length that is greater than a distance from the attachment location to the proximal end of the interventional device when the interventional device is attached to the catheter shaft. The at least one flexible element in the collapsed configuration can be configured to extend over the proximal end of the interventional device when the interventional device is attached to the catheter shaft.

In general, in one embodiment, a delivery system for an interventional device includes an elongate catheter body having a first magnet on a distal end thereof, a catheter shaft extending within the catheter body and configured to releasably attach to the interventional device, and a second magnet at a distal portion of the catheter shaft. The first and second magnets are configured to repel one another to provide a tactile stop when the catheter shaft is moved proximate to a distal end of the elongate catheter body.

This and other embodiments can include one or more of the following features. The distal portion can include a cylindrical tip of the catheter shaft, and the cylindrical tip can have a larger diameter than a proximal portion of the catheter shaft. The elongate catheter body can be a steerable elongate catheter body. The elongate catheter body can include a plurality of cables configured to be activated to steer the elongate catheter body. The elongate catheter body can be the only steerable elongate catheter body in the delivery system.

In general, in one embodiment, a method of delivering an interventional device, includes: (1) moving a catheter shaft distally relative to an elongate catheter body until the interventional device extends out of a distal end of the elongate catheter body; (2) pulling the catheter shaft proximally with a first a first amount of force until at least one flexible element in an expanded configuration and at a distal portion of the catheter shaft engages with the distal end of the elongate body and a tactile response is felt; (3) maintaining the at least one flexible element in the expanded configuration distal to the distal end of the elongate body while positioning the interventional device in a body; and (4) pulling the catheter shaft proximally with a second amount of force that is greater than the first amount of force so as to collapse the at least one flexible element to a collapsed configuration to bring the at least one flexible element into the elongate catheter body.

This and other embodiments can include one or more of the following features. The moving step can further include moving the catheter shaft distally relative to the elongate catheter body until the at least one flexible element is distal of the distal end of the elongate catheter body. The method can further include allowing the at least one flexible element to self-expand after the step of moving the catheter shaft distally. The at least one flexible element can include two flexible elements, and the two flexible elements can be positioned opposite one another about the distal portion of the catheter shaft. The distal portion can include a cylindrical tip of the catheter shaft, the cylindrical tip having a larger diameter than a proximal portion of the catheter shaft. The at least one flexible element can be a looped element extending from the distal portion of the catheter shaft. The at least one flexible element can be a tab extending from the distal portion of the catheter shaft. The at least one flexible element can be an annular ring extending around the distal portion of the catheter shaft. The at least one flexible element can be a spring-activated ball bearing. The at least one flexible element can include a polymer. The at least one flexible element can include a shape memory alloy. The at least one flexible element can include stainless steel. The method can further include actively steering the elongate catheter body such that the interventional device reaches a desired location in the body. Actively steering can include steering using a plurality of cables extending within the elongate catheter body. Pulling the catheter shaft proximally with a second amount of force can include allowing the at least one flexible element to collapse over a proximal end of the interventional device, and the method can further include guiding the interventional device into the elongate catheter body with the flexible element collapsed over the proximal end of the interventional device.

In general, in one embodiment, a delivery system for an interventional device includes an elongate catheter body, a catheter shaft extending within the catheter body and configured to releasably attach to the interventional device, and at least one flexible element attached to a distal portion of the catheter shaft at an attachment location. The at least one flexible element has a collapsed configuration and an expanded configuration. The at least one flexible element in the expanded configuration extends further radially outwards than the at least one flexible element in the collapsed configuration, and the flexible element in the collapsed configuration has a length that is greater than a distance from the attachment location to a proximal end of the interventional device when the interventional device is attached to the catheter shaft. The at least one flexible element is configured to collapse from the expanded configuration to the collapsed configuration when moved relative to and against the distal end of the elongate body. The at least one flexible element in the collapsed configuration extends over the proximal end of the interventional device when the interventional device is attached to the catheter shaft.

This and other embodiments can include one or more of the following features. The at least one flexible element can be configured to self-expand from the collapsed configuration to the expanded configuration when released from the elongate catheter body. The at least one flexible element can include two flexible elements, and the two flexible elements can be positioned opposite one another about the distal portion of the shaft. The distal portion can include a cylindrical tip of the catheter shaft, and the cylindrical tip can have a larger diameter than a proximal portion of the catheter shaft. The at least one flexible element can be a looped element extending from the distal portion of the catheter shaft. The at least one flexible element can be a tab extending from the distal portion of the catheter shaft. The at least one flexible element can include a polymer. The at least one flexible element can include a shape memory alloy. The at least one flexible element can include stainless steel. The at least one flexible element in the expanded configuration can extend beyond an outer circumference of the elongate catheter body. The at least one flexible element in the expanded configuration can further be configured to provide a tactile stop when moved proximally relative to and against a distal end of the elongate catheter body with a first amount of force. The flexible element can be configured to collapse from the expanded configuration to the collapsed configuration when the flexible element is moved relative to and against the distal end of the elongate catheter body with a second amount of force that is greater than the first amount of force.

In general, in one embodiment, a method of retracting an interventional device, includes: (1) moving a catheter shaft relative to an elongate catheter body until at least one flexible element at a distal end of the catheter shaft engages with a distal end of the elongate body; (2) continuing to move the catheter shaft and elongate catheter body relative to one another until the at least one flexible element collapses over a proximal end of an interventional device attached to the delivery device; and (3) guiding the interventional device into the elongate catheter body with the at least one flexible element collapsed over the proximal end of the interventional device.

This and other embodiments can include one or more of the following features. The at least one flexible element can include two flexible elements, and the two flexible elements can be positioned opposite one another about the distal portion of the catheter shaft. The distal portion can include a cylindrical tip of the catheter shaft, and the cylindrical tip can have a larger diameter than a proximal portion of the catheter shaft. The at least one flexible element can be a looped element extending from the distal portion of the catheter shaft. The at least one flexible element can be a tab extending from the distal portion of the catheter shaft. The at least one flexible element can include a polymer. The at least one flexible element can include a shape memory alloy. The at least one flexible element can include stainless steel. The at least one flexible element in the expanded configuration can extend beyond an outer circumference of the elongate catheter body. The method can further include: (1) pulling the catheter shaft proximally with a first a first amount of force until the at least one flexible element in an expanded configuration and at a distal portion of the catheter shaft engages with a distal end of the elongate body and a tactile response is felt; and (2) maintaining the at least one flexible element in the expanded configuration distal to the distal end of the elongate body while positioning the interventional device in a body. The step of continuing to move the catheter shaft and elongate catheter body relative to one another until the flexible element collapses over a proximal end of an interventional device attached to the delivery device can include pulling the catheter shaft proximally with a second amount of force that is greater than the first amount of force.

In general, in one embodiment, a delivery system for an interventional device includes an elongate catheter body, a catheter shaft extending within the catheter body and configured to releasably attach to the interventional device, at least one flexible element attached to a distal portion of the catheter shaft, and an activation element. The at least one flexible element has an expanded configuration in which the at least one flexible element extends beyond an outer circumference of the elongate catheter body and a collapsed configuration in which the at least one flexible element collapses within the elongate catheter body. The activation element is configured to expand the at least one flexible element to the expanded configuration and collapse the at least one flexible element to the collapsed configuration.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 17A-17B show an exemplary delivery device with flexible arms for enhanced retraction of a mitral valve clip.

FIGS. 19A-19D show an exemplary embodiment of a delivery device with flexible arms.

FIGS. 20A-20B show an exemplary embodiment of a delivery device with flexible arms.

FIGS. 21A-21B show an exemplary embodiment of a delivery device with flexible arms.

FIGS. 22A-22B show an exemplary embodiment of a delivery device with flexible arms.

DETAILED DESCRIPTION

Described herein is a delivery system that can be used, for example, with a mitral valve leaflet apposition device, such as a mitral valve clip. The delivery system can include extensions thereon that can be used as a stop for tactile feedback to a physician and/or as a retraction aid for retracting the leaflet apposition device.

Figure 1A:
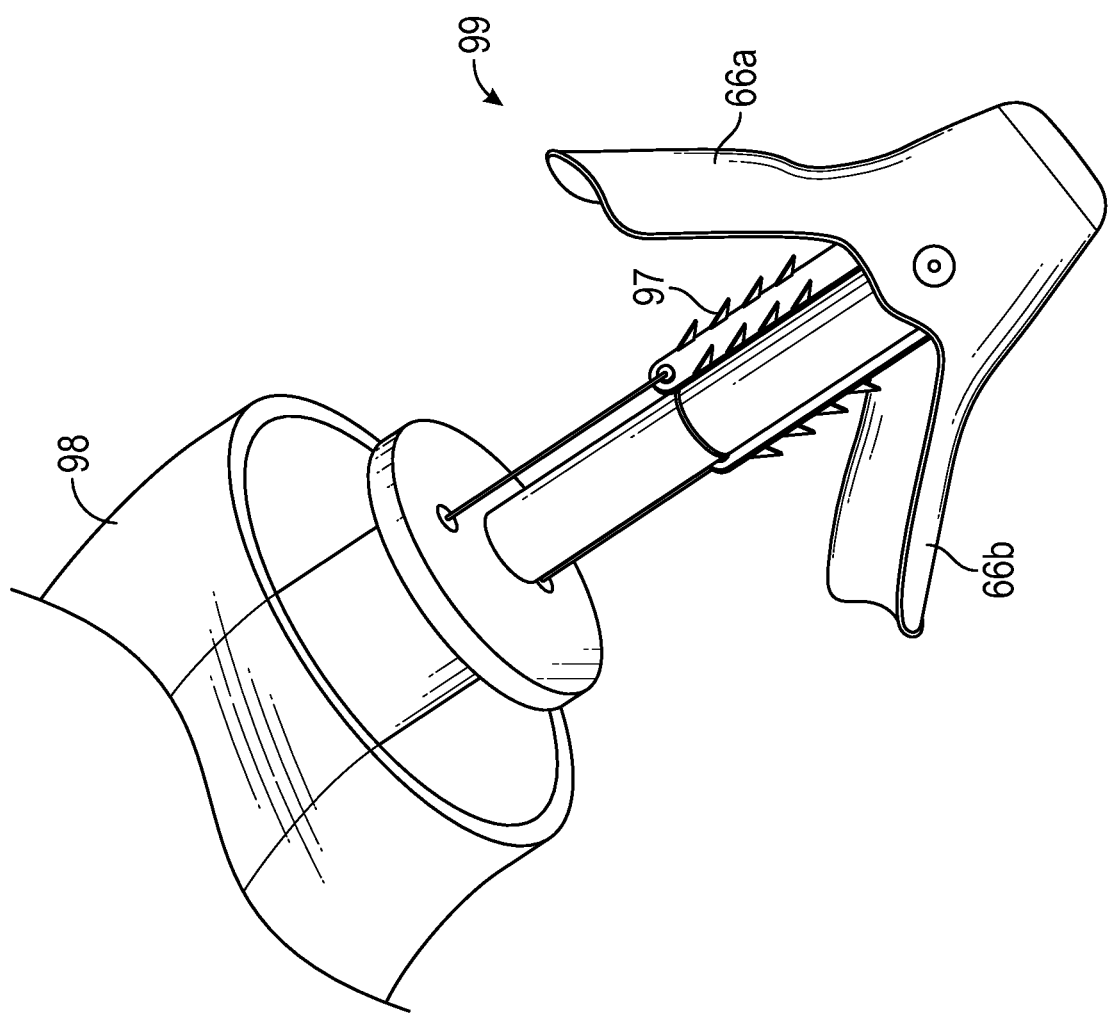
FIG. 1A shows an exemplary mitral valve clip and delivery system.
Figure 1B:
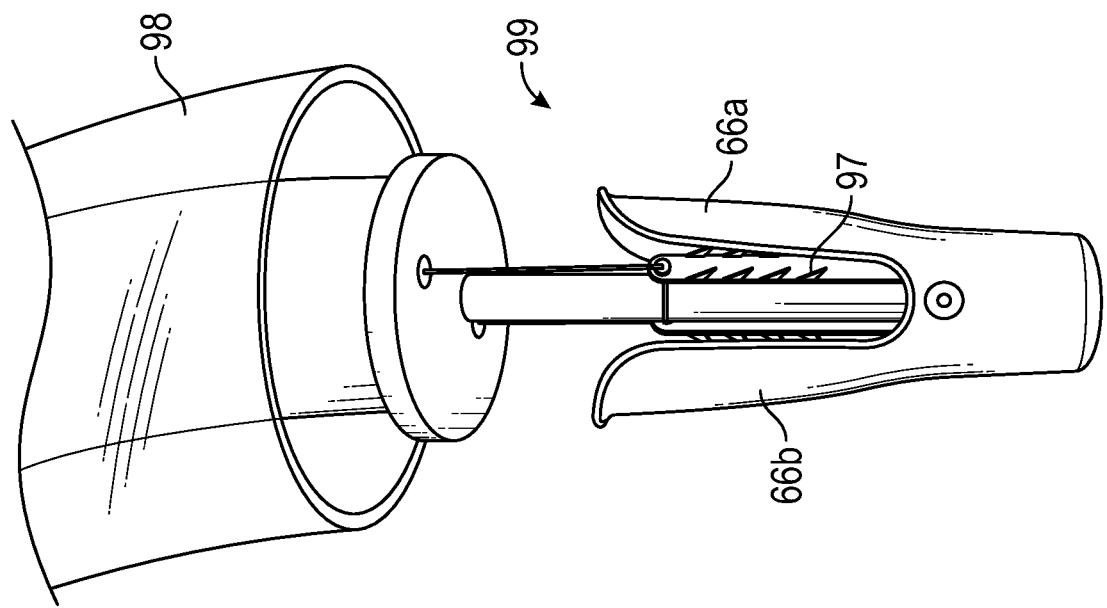
FIG. 1B shows the arms of a mitral valve clip collapsed for delivery or retraction.
Figure 2:
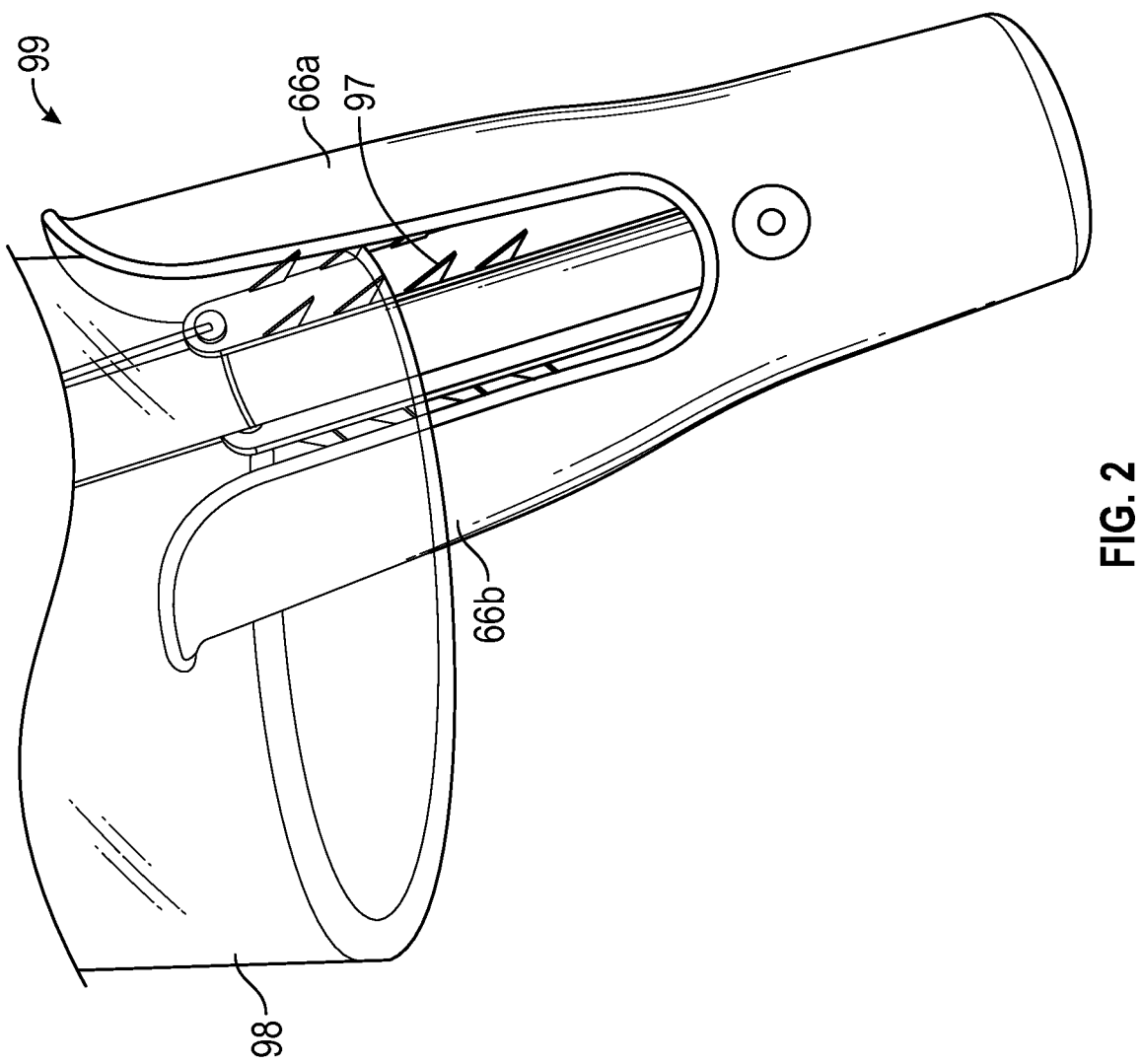
FIG. 2 shows how an arm of a mitral valve clip can get caught on the guiding catheter of a delivery device.
Figure 3:
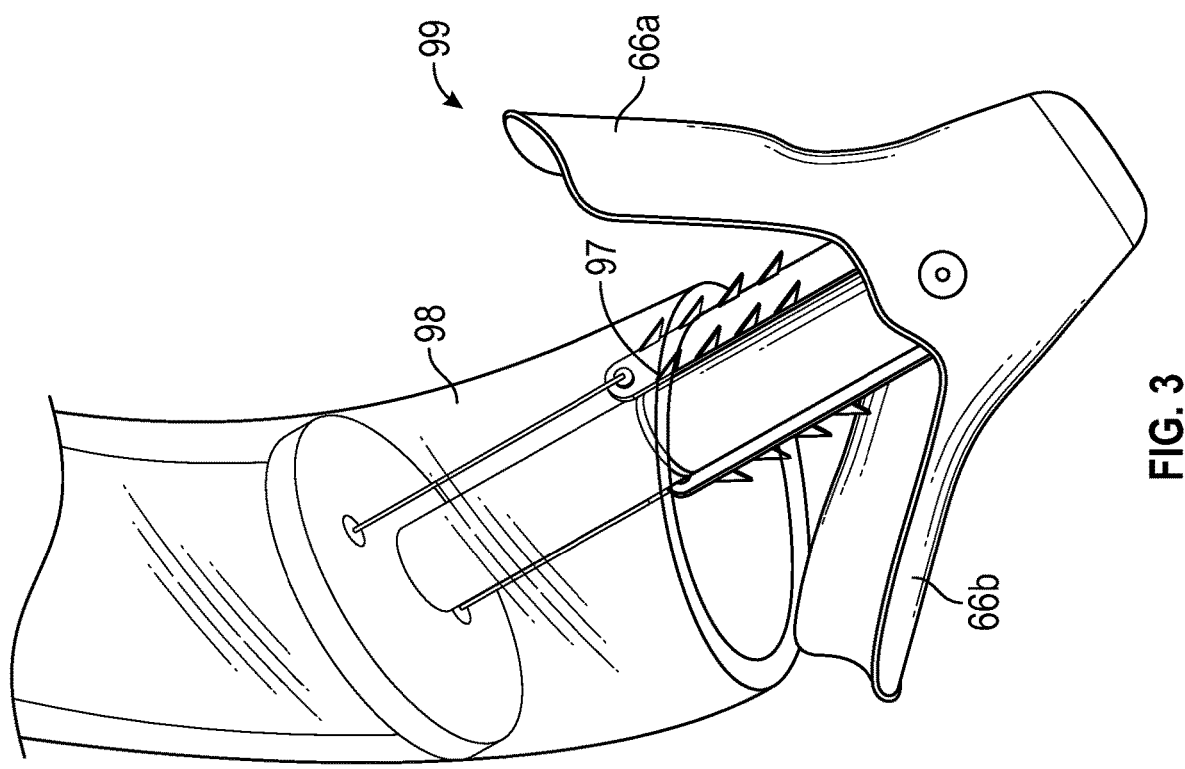
FIG. 3 shows how the barbed grippers of a mitral valve clip can get caught on the guiding catheter of a delivery device.
Figure 4B:
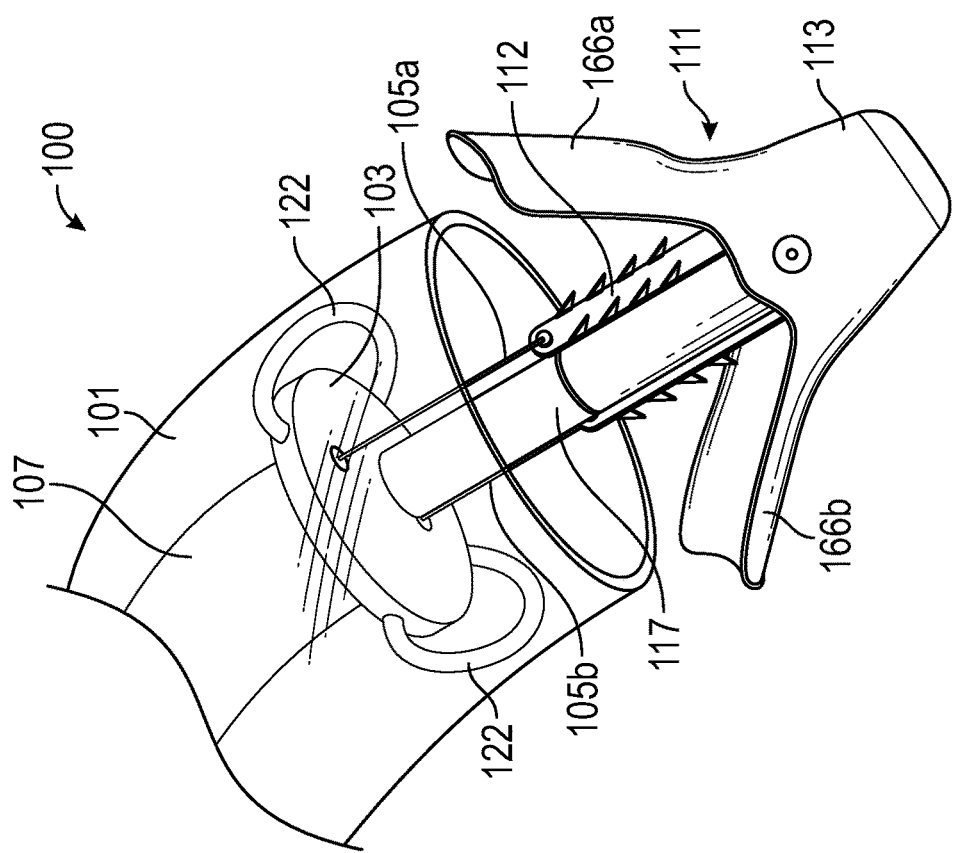
FIGS. 4A-4B show a single catheter steerable delivery system with a flexible stop as described herein.
Figure 4A:
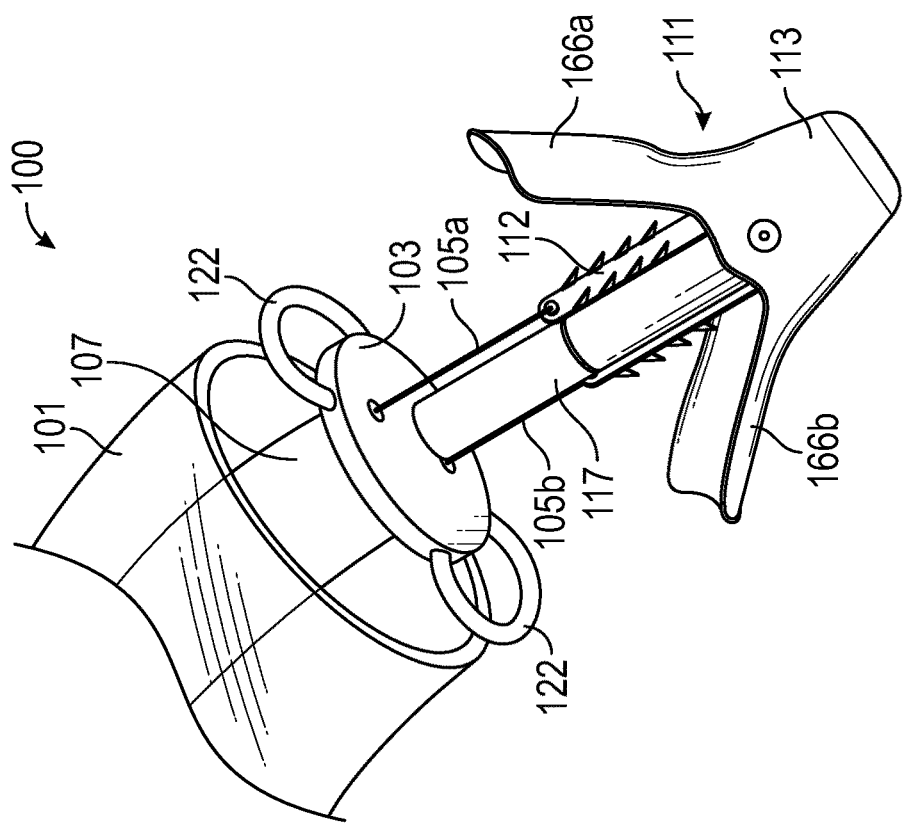

Referring to FIGS. 4A and 4B, an exemplary single catheter steerable delivery system 100 for a device, such as a mitral valve leaflet apposition device 111, is shown. As shown in FIGS. 4A-4B, the delivery system 100 includes an outer hollow elongate body 101 and a catheter shaft 107 extending therein. The outer elongate body 101 can be steerable through use of a plurality of cables or tethers, as shown in FIGS. 16A-16E.

Figure 16A:
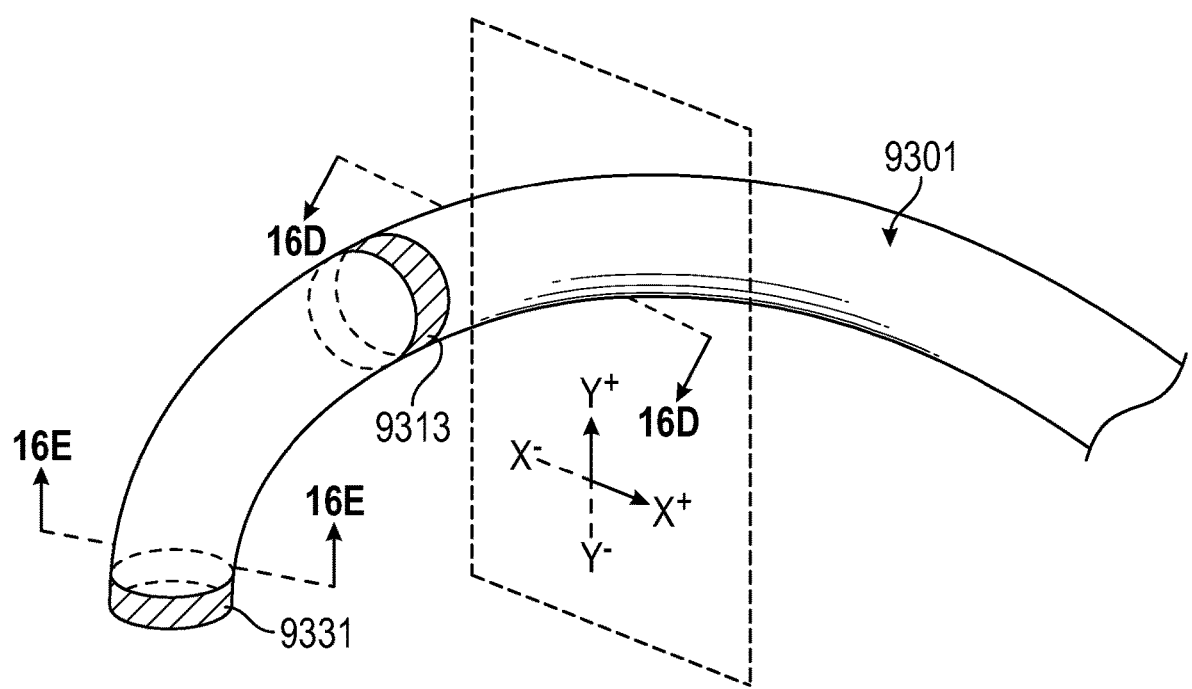
FIGS. 16A-16E show a steering mechanism for a single catheter steerable delivery system.
Figure 16B:
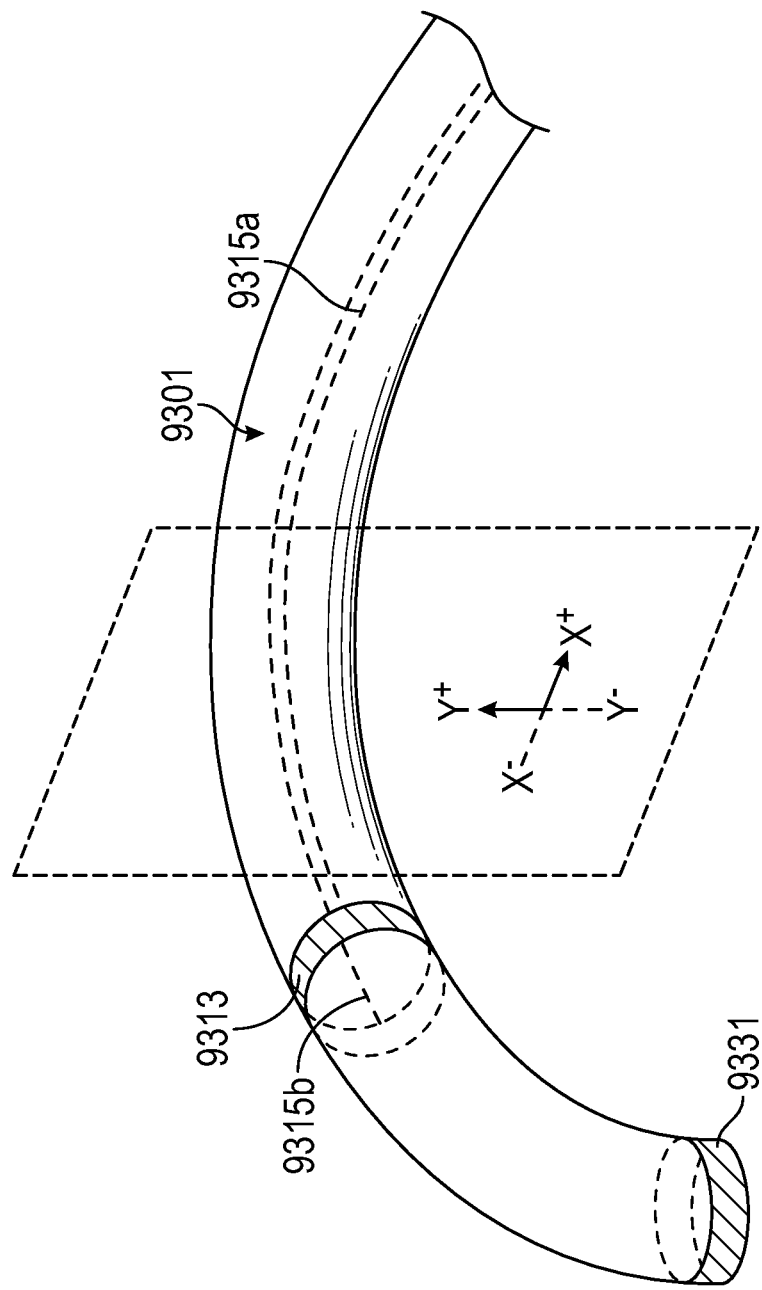
Figure 16C:
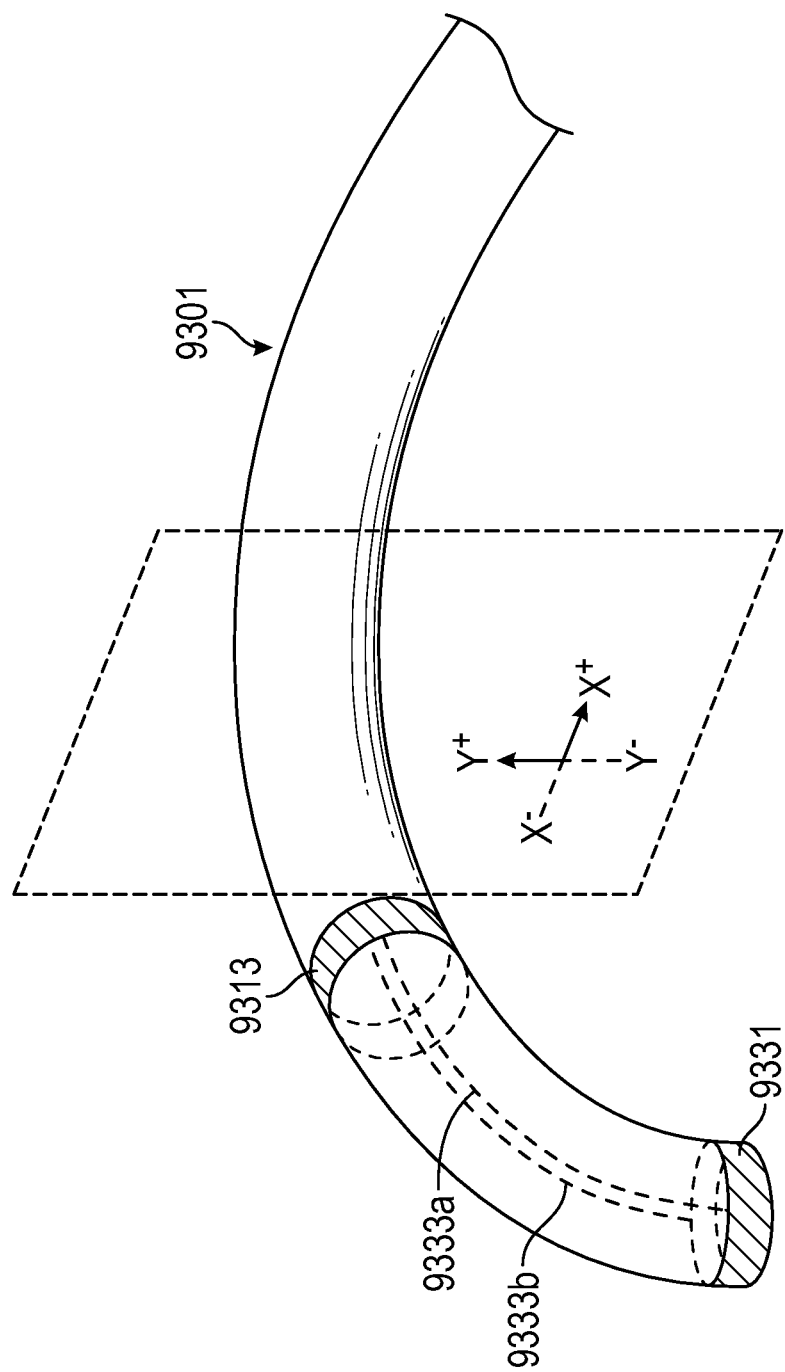
Figure 16D:
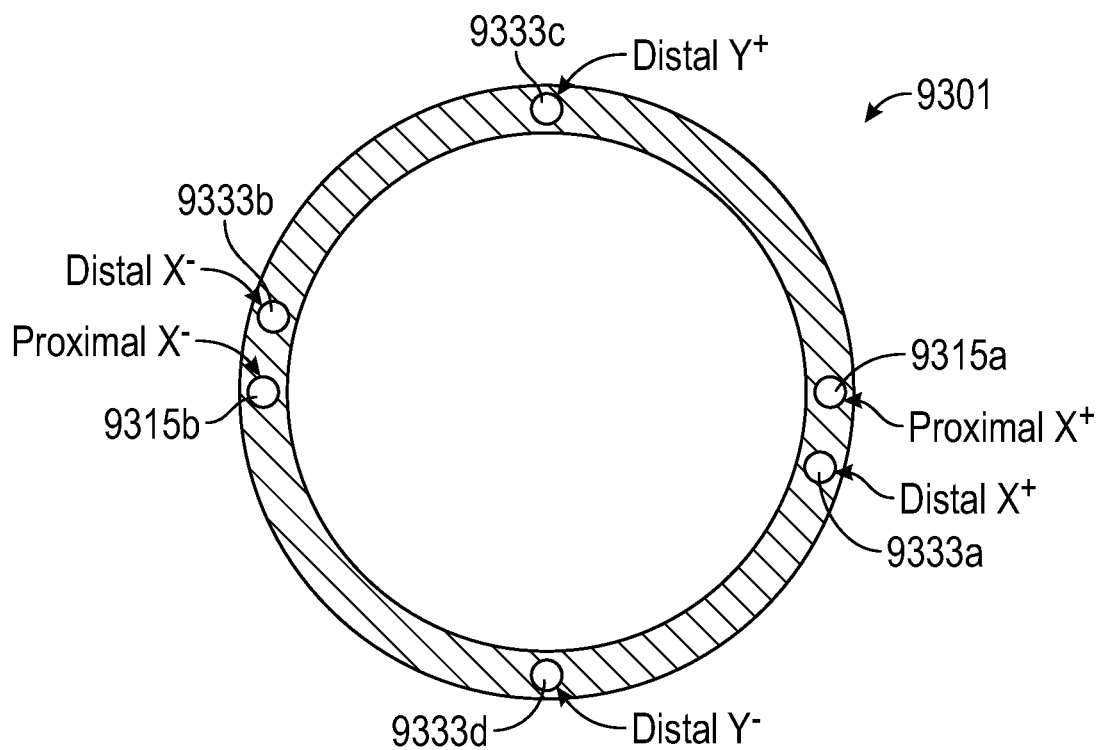
Figure 16E:
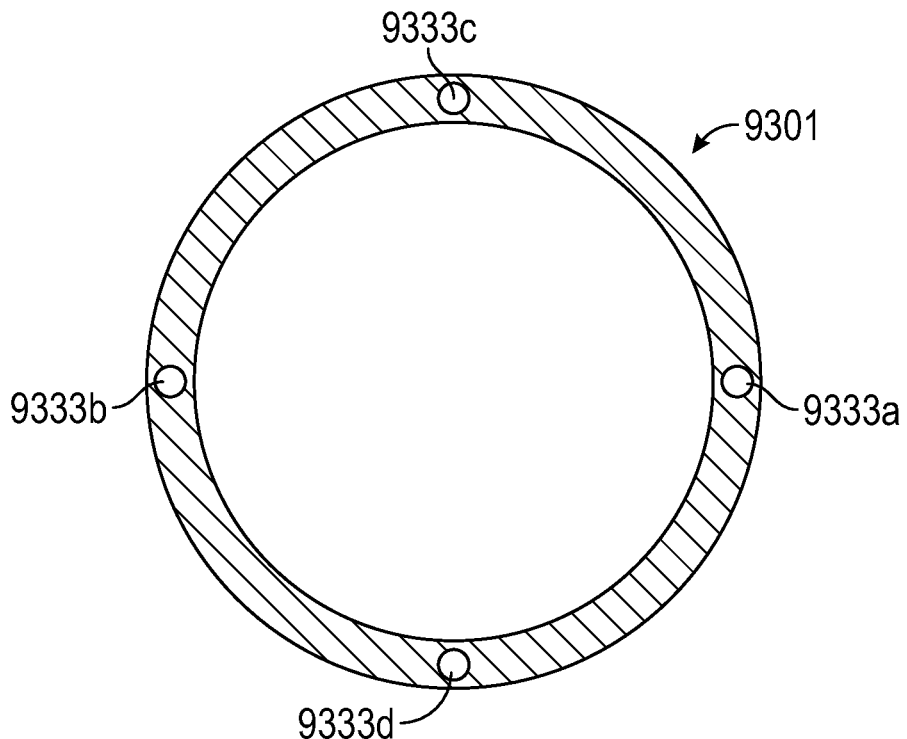
Figure 18A:
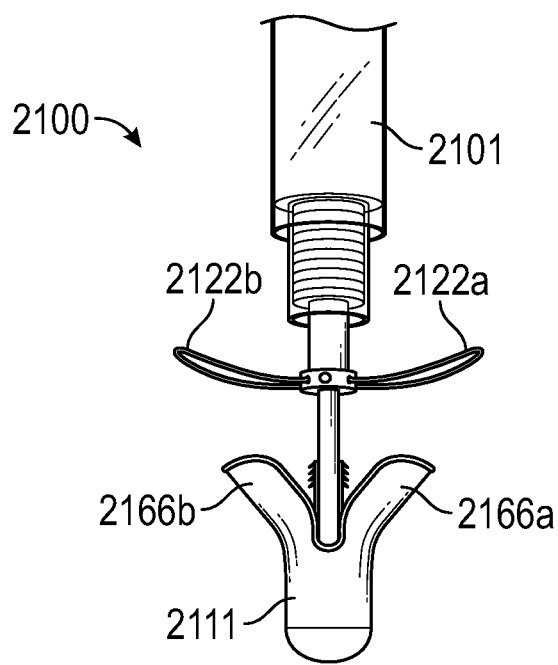
FIGS. 18A-18D show use of an exemplary delivery device with flexible arms to retract a mitral valve clip.
Figure 18B:
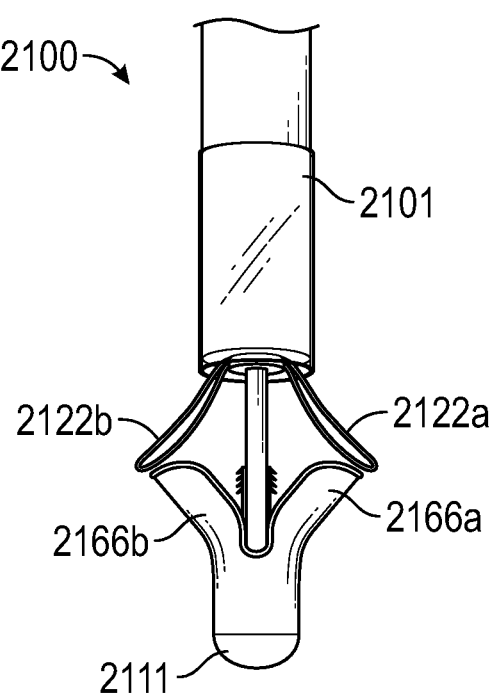
Figure 18C:
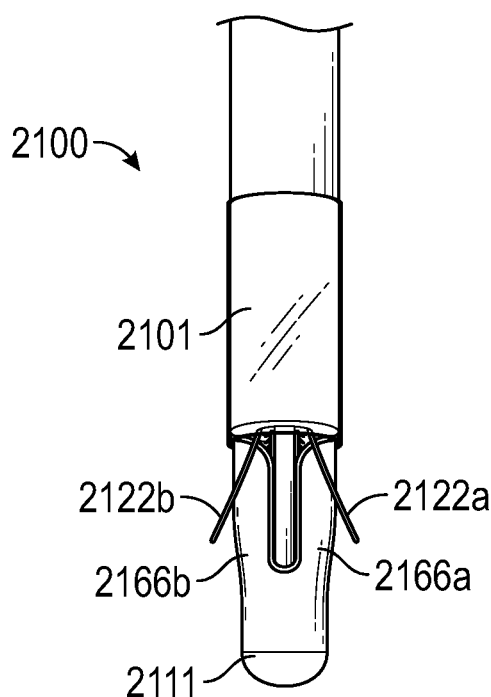
Figure 18D:
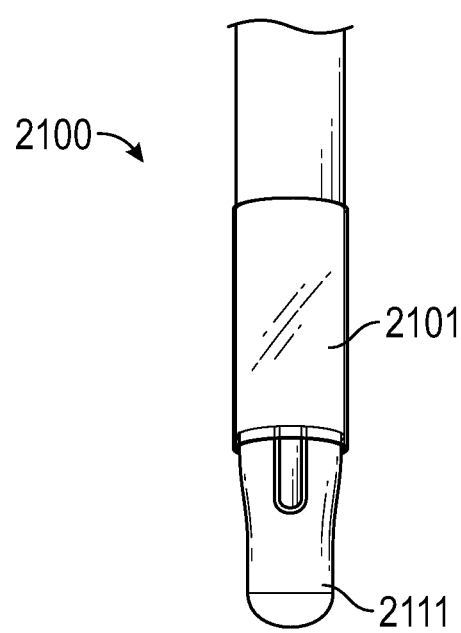

Referring to FIGS. 16A-16E, an outer elongate body 9301 can include a distal annular ring 9331 and a proximal annular ring 9313. A plurality of cables 9333a-d (only 9333a,b are shown in FIG. 16C for clarity) can extend from the proximal end of the elongate body 9301 to the distal annular ring 9331. Similarly, a plurality of cables 9315a,b can extend from the proximal end of the elongate body 9301 to the proximal annular ring 9313. The distal ring 9331 and the cables 9333a-d connected thereto can control a distal curve in the elongate body 9301 and can provide bending in the X+, X−, Y+, and Y− directions by tensioning one or more of the cables 9333a-d. Further, the proximal ring 9313 and the cables 9315a,b connected thereto can control a proximal curve in the elongate body 9301 and can provide bending in the X+ and X-directions by tensioning one or more of the cables 9315a,b.

Referring back to FIGS. 4A-4B, a coupling shaft 117 extends from the catheter shaft 107 for attachment to the apposition device 111 through a coupling mechanism, such as a friction fit or locking element. Further, the inner diameter of the elongate body 101 is sized such that the mitral valve leaflet apposition device 111 can be attached to the coupling shaft 117, placed in a delivery configuration (i.e., with the arms 166a,b closed), and then advanced through the elongate body 101 from the proximal end of the elongate body 101 to the distal end of the elongate body 101 (e.g., by pushing on the catheter shaft 107).

The delivery system 100 further includes a cylindrical tip 103 positioned between the catheter shaft 107 and coupling shaft 117. Tether lines 105a,b can extend therethrough for connection to the barbed grippers 112 of the device 111. The tether lines 105a,b can be configured to tighten to pull the barbed grippers 112 proximally and against the coupling shaft 117 or to loosen to allow the barbed grippers 112 to move distally and away from the shaft 117 (e.g., into grasped tissue). The cylindrical tip 103 further includes a stop 122 (here shown as two separate flexible looped extensions). The stop 122 can be attached to the cylindrical tip 103 such that it sits proximal to the coupling shaft 117 (and to the apposition device 111 when the device 111 is attached to the delivery system 100). In other embodiments, the stop 122 can be positioned just proximal or distal to the cylindrical tip 103 and/or can be attached to the distal end of the elongate body 101. Further, the stop 122 can have an expanded configuration that extends past the outer circumference of the elongate body 101. For example, as shown in FIG. 4A, the two looped extensions of the stop 122 can be attached to the cylindrical tip 103 such that they are directly opposite one another. In this embodiment, each of the looped extensions can extend beyond the outer circumference of the elongate body 101. Thus, the diameter or radial length of the cylindrical tip 103 and the stop 122 can be greater than the diameter of the elongate body 101. In other embodiments, only one looped extension can extend beyond the outer circumference. Further, in some embodiments, the looped extensions can be spaced unequally around the circumference of the cylindrical tip 103 (and thus not directly opposite one another). Further, in some embodiments, there an be three or more looped extensions equally or unequally spaced around the circumference of the cylindrical tip 103. Further, the extensions of the stop 122 need not be looped, but can instead be cantilevered extensions. The stop 122 can further be configured to flex or bend to a low profile when inserted or retracted into the elongate body 101.

The size of the stop 122 can be such that it is collapsible to a dimension of 3-8 mm, preferably about 5.5 mm, in order to fit inside the inner diameter of the elongate body 101. In its expanded configuration, the size of the stop 122 can be larger than the outer diameter of the elongate body 101, and can have a radial length ('wingspan') of about 6-12 mm, e.g., about 9 mm.

The stop 122 can thus flex or bend to a low profile or diameter when inserted or retracted into the elongate body 101 and expand to a larger profile or diameter when outside of the elongate body 101. The stop 122 in the expanded configuration can provide tactile feedback to the user (e.g., physician) when pulled against the distal tip of the elongate body 101, thereby: (1) providing an indication that the device 111 is fully extended outside of the elongate body 101 before releasing the clip arms 166a,b; and (2) and preventing the user from pulling the barbs 112 into the elongate body 101, which might otherwise catch on the inner diameter of the elongate body 101. When pulled proximally with sufficient force (i.e., greater than the amount of force used when identifying positioning of the stop 122), however, the stop 122 can flex, bend, or otherwise change shape in order to allow the tip 103, and coupling shaft 117, to be pulled back into the elongate catheter body 101 (as shown in FIG. 4B). This might be useful, for example, after the apposition device 111 has been deployed and the delivery system 100 is being removed from the body.

The stop 122 can be positioned such that it does not interfere with the clip arms 166a,b of the device 111 when the arms 166a,b are closed. That is, the distance between the stop 122 (in the expanded configuration) and the distal tip of the device 111 can be greater than the distance between the proximal tip of the arms 166a,b in the closed configuration and the distal tip of the device 111. Advantageously, this allows the apposition device 111 to be fully closed and retracted back into the elongate body 101 (e.g., for removal from the patient) if desired. In some embodiments, the stop 122 can be integrated into the tip 103. In other embodiments, the stop 12 can be attached to or integrated with the elongate catheter body 101, such as be positioned within the inner diameter of the elongate catheter body 101 (such that interaction of the stop with the cylindrical tip 103 rather than the elongate body 101 provides the desired tactile feedback).

Figure 5A:
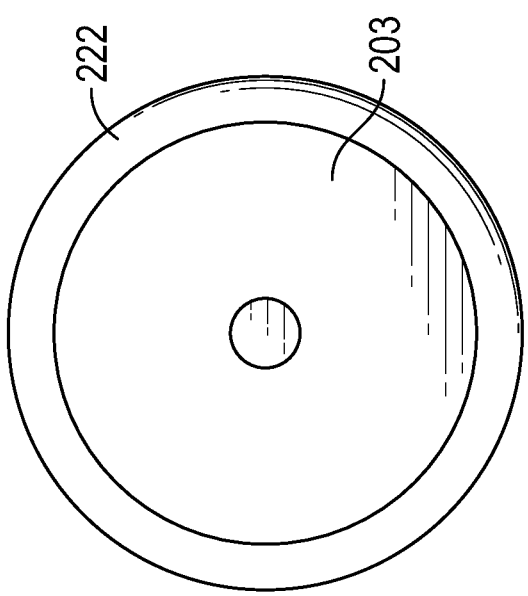
FIGS. 5A-5B show an exemplary flexible stop.
Figure 5B:
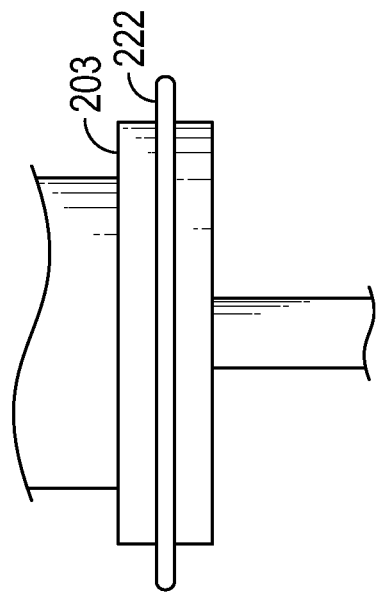
Figure 6A:
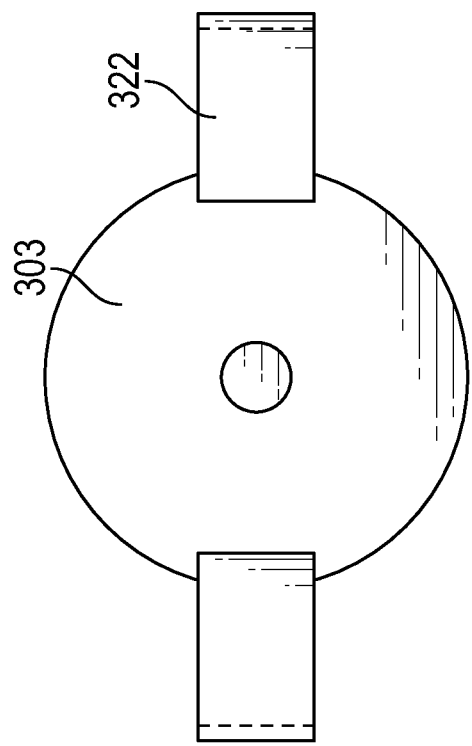
FIGS. 6A-6B show another exemplary flexible stop.
Figure 6B:
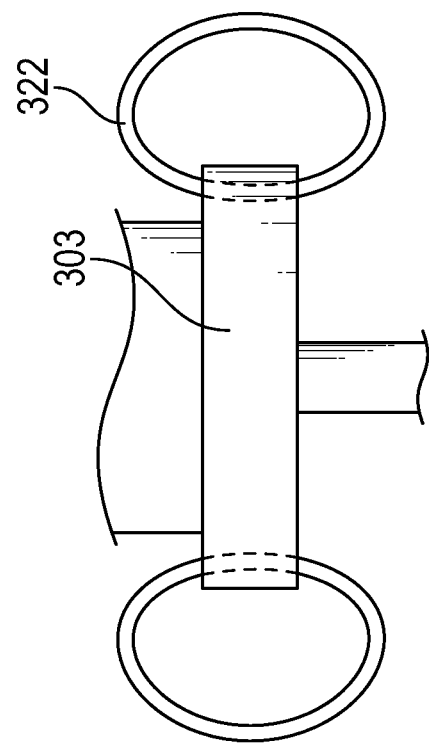
Figure 8A:
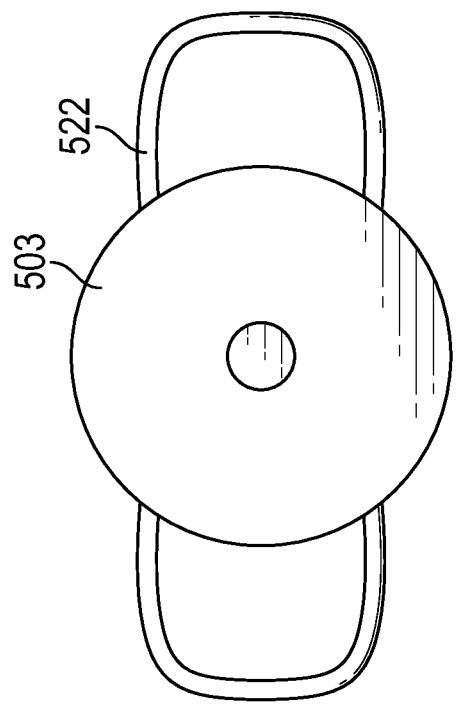
FIGS. 8A-8B show another exemplary flexible stop.
Figure 8B:
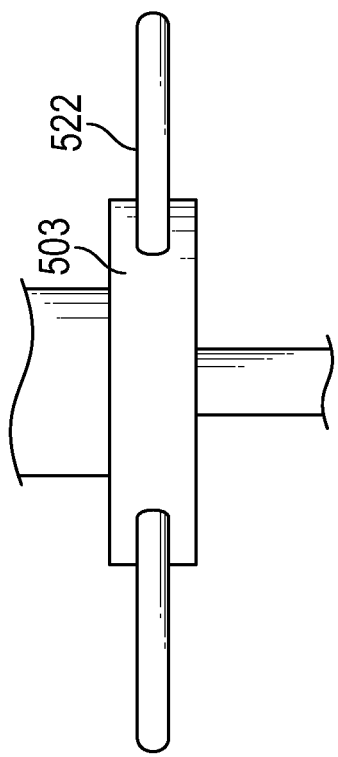
Figure 7A:
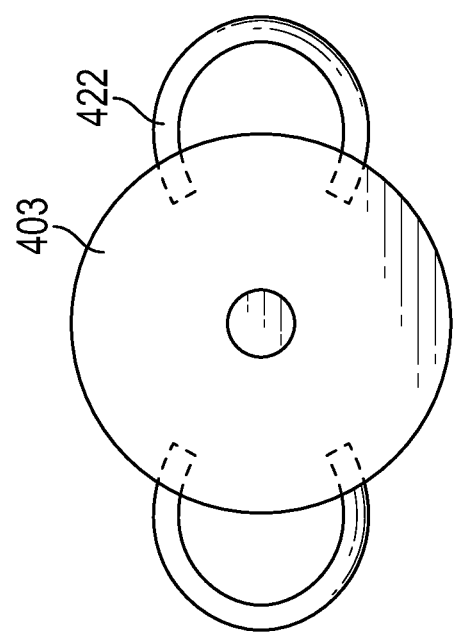
FIGS. 7A-7B show another exemplary flexible stop.
Figure 7B:
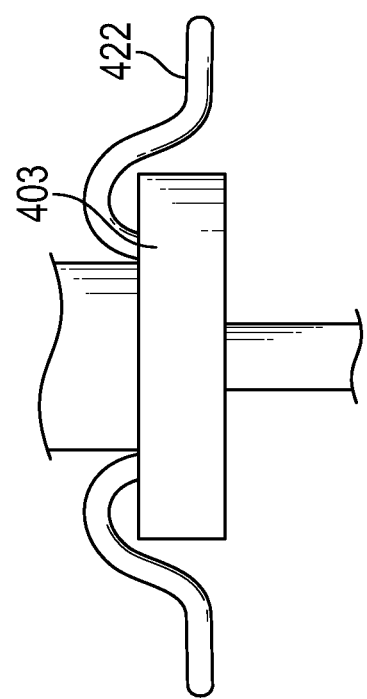
Figure 10B:
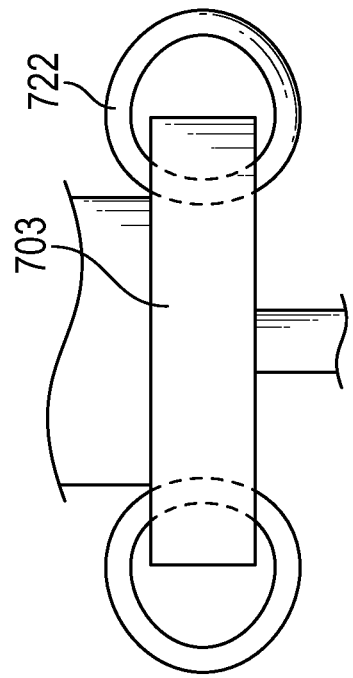
FIGS. 10A-10B show another exemplary flexible stop.
Figure 10A:
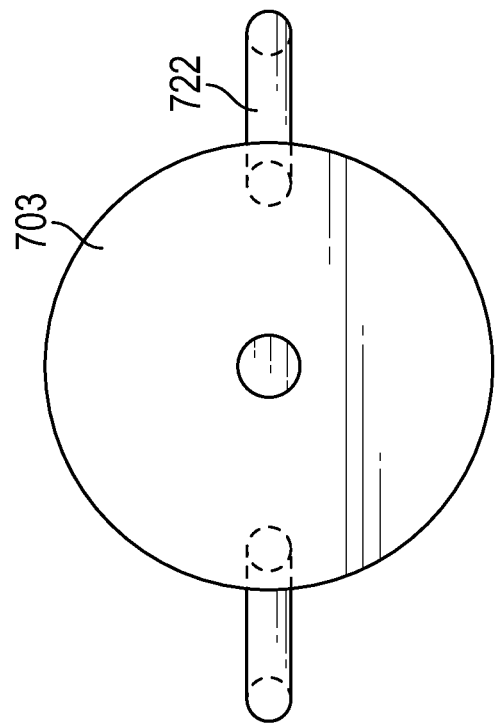
Figure 9B:
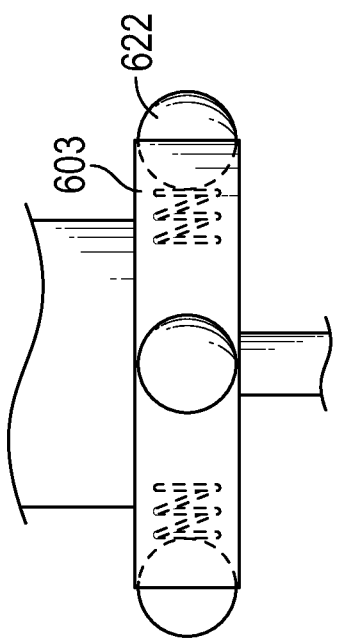
FIGS. 9A-9B show another exemplary flexible stop.
Figure 9A:
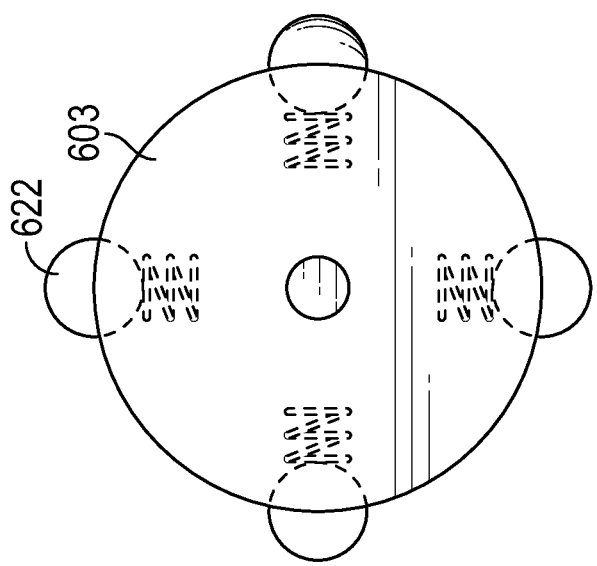
Figure 12A:
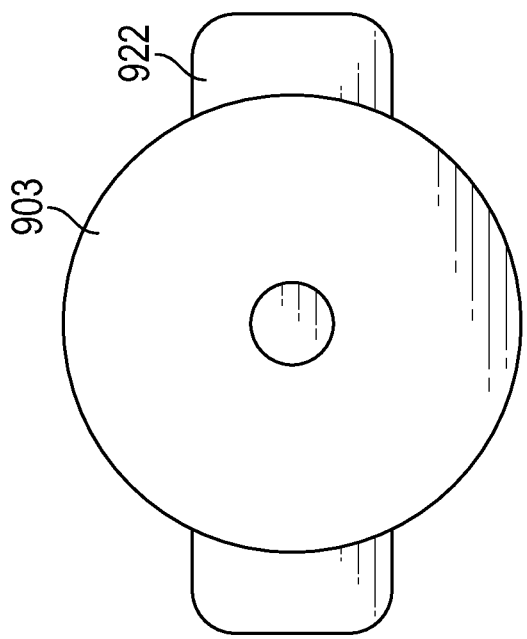
FIGS. 12A-12B show another exemplary flexible stop.
Figure 12B:
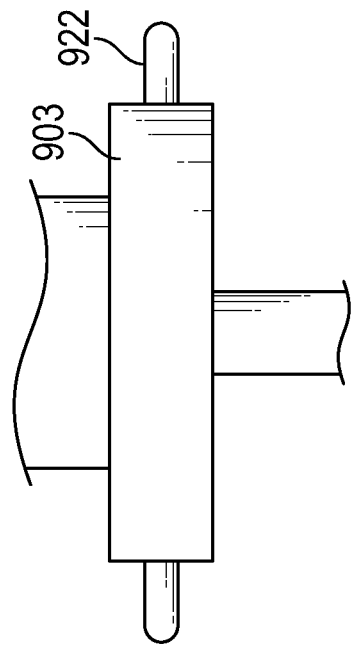
Figure 11A:
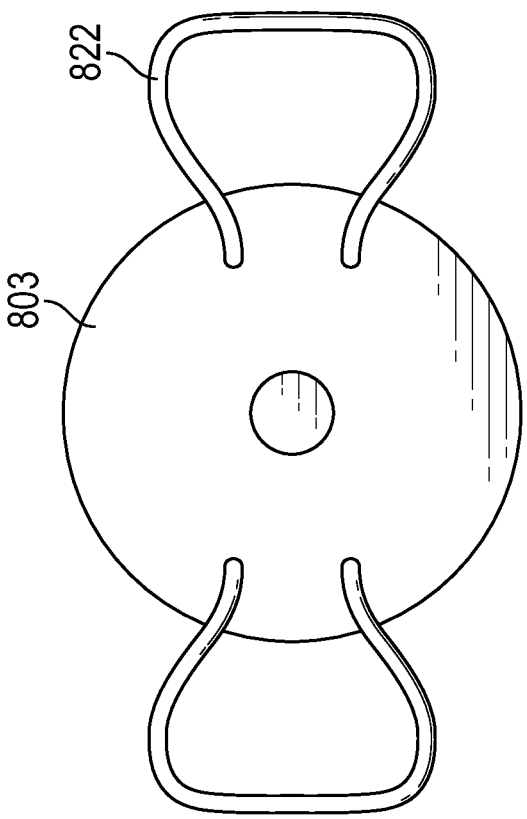
FIGS. 11A-11B show another exemplary flexible stop.
Figure 11B:
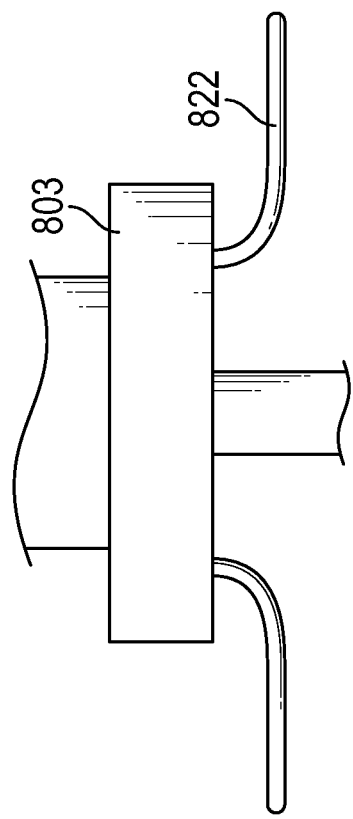

Other stop designs are possible while still providing the same advantages as stop 122. All of the stop designs described herein can either have a diameter or radial length that is greater than the diameter of the elongate body or can otherwise have an extension that extends beyond the circumference of the elongate body. Additionally, all of the stop designs can be flexible enough to flex, bend, or otherwise change shape to fit within the elongate body. For example, as shown in FIGS. 5A and 5B, a stop 222 can be a flexible annular ribbon extending around the cylindrical tip 203. As shown in FIGS. 6A and 6B, the stop 322 can include two or more flexible ring or cuff members attached to the tip 303 such that the central axes of the cuffs are parallel to the plane of the tip 303. As shown in FIGS. 7A and 7B, the stop 422 can include looped extensions attached to the tip 403. The looped extensions can, for example, be bent or flared along the central axis of the tip 403, as shown in FIG. 7B. As shown in FIGS. 8A and 8B, the stop 522 can include looped extensions extending straight out (radially) from the tip 503. The looped extensions of the stop 522 can have a flattened or rounded square/rectangle profile. Referring to FIGS. 9A and 9B, the stop 622 can include a plurality of springactuated ball bearings positioned around the circumference of the tip 603. As shown in FIGS. 10A and 10B, the stop 722 can include two or more thin rings (e.g., wire rings) attached to the cylindrical tip 703 such that the central axes of the rings are parallel to the plane of the tip 703. As shown in FIGS. 11A and 11B, the stop 822 can include looped extensions that extend from the distal end of the cylindrical tip 803 and flare radially outwards just distal to the cylindrical tip 803. As shown in FIGS. 12A and 12B, the stop 922 can include tabs that extend radially outwards from the cylindrical tip 903.

In any of the embodiments described herein, the flexible extensions can be made of round wire or flat wire ('ribbon'). The flexible elements can further be made of polymer or metal, stainless steel, nitinol, or other shape memory alloy. The material for the flexible extensions can be selected such that the flexible extensions can bend without cracking, breaking, or plastically deforming.

Figure 15:
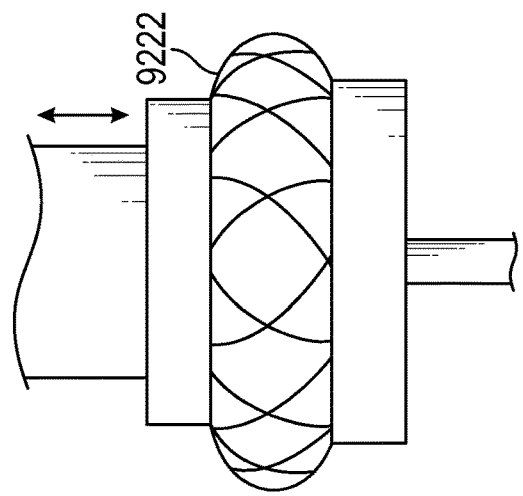
FIG. 15 shows an expandable cage flexible stop.

Referring to FIG. 15, in some embodiments, the stop 9222 can be an expandable annular woven or braided cage (e.g., made of woven or braided wire or fibers).

Figure 14:
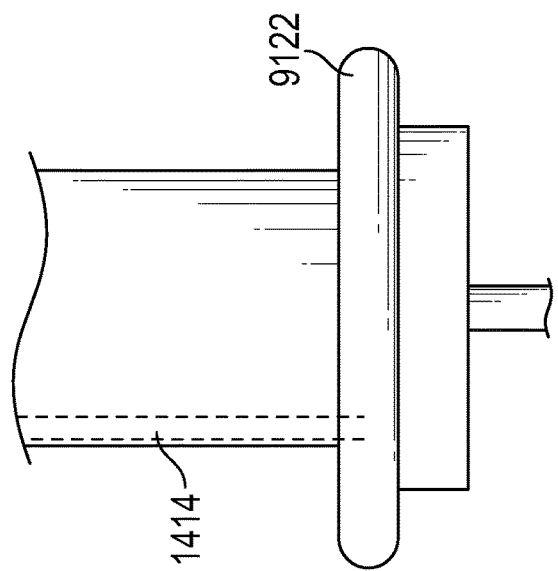
FIG. 14 shows an inflatable stop.
Figure 13:
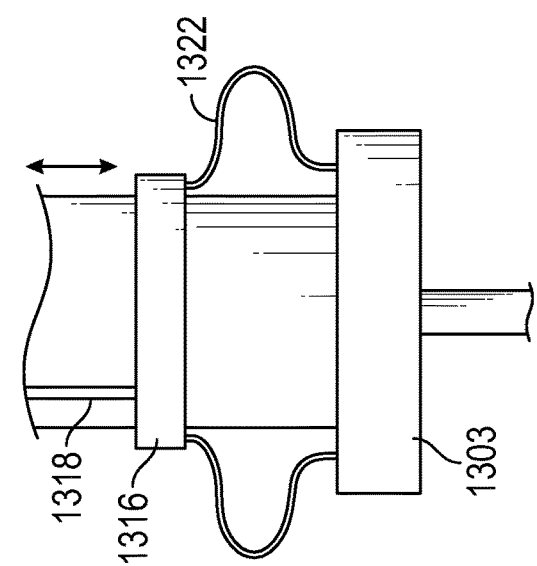
FIG. 13 shows manual actuation of a flexible stop.

In many embodiments, the stops described herein can be passively actuated (e.g., can self-expand automatically when the stop is removed from the elongate body). In other embodiments, shown in FIGS. 13 and 14, the physician can actively actuate the stop by adjusting a control on the proximal end of the delivery system. For example, as shown in FIG. 13, the stop 1322 can include two looped extensions, each of which is attached at the distal end to the cylindrical tip 1303 and at the proximal end to a slideable proximal ring 1316. A control wire 1318 can be connected to the proximal ring 1316 to move the ring 1316 relative to the longitudinal axis. Distal movement of the wire 1318 and ring 1316 will flare the looped extensions of the stop 1322 outwards while proximal movement of wire 1318 and ring 1316 will flatten or contract the looped extensions. Similarly, as shown in FIG. 14, the stop 1922 can be an inflatable element (e.g., one or more inflatable rings, cuffs, or looped extensions). In such an embodiment, an inflation lumen 1414 can traverse the length of the delivery catheter shaft to provide inflation fluid thereto for active inflation of the stop 1922.

Figure 29:
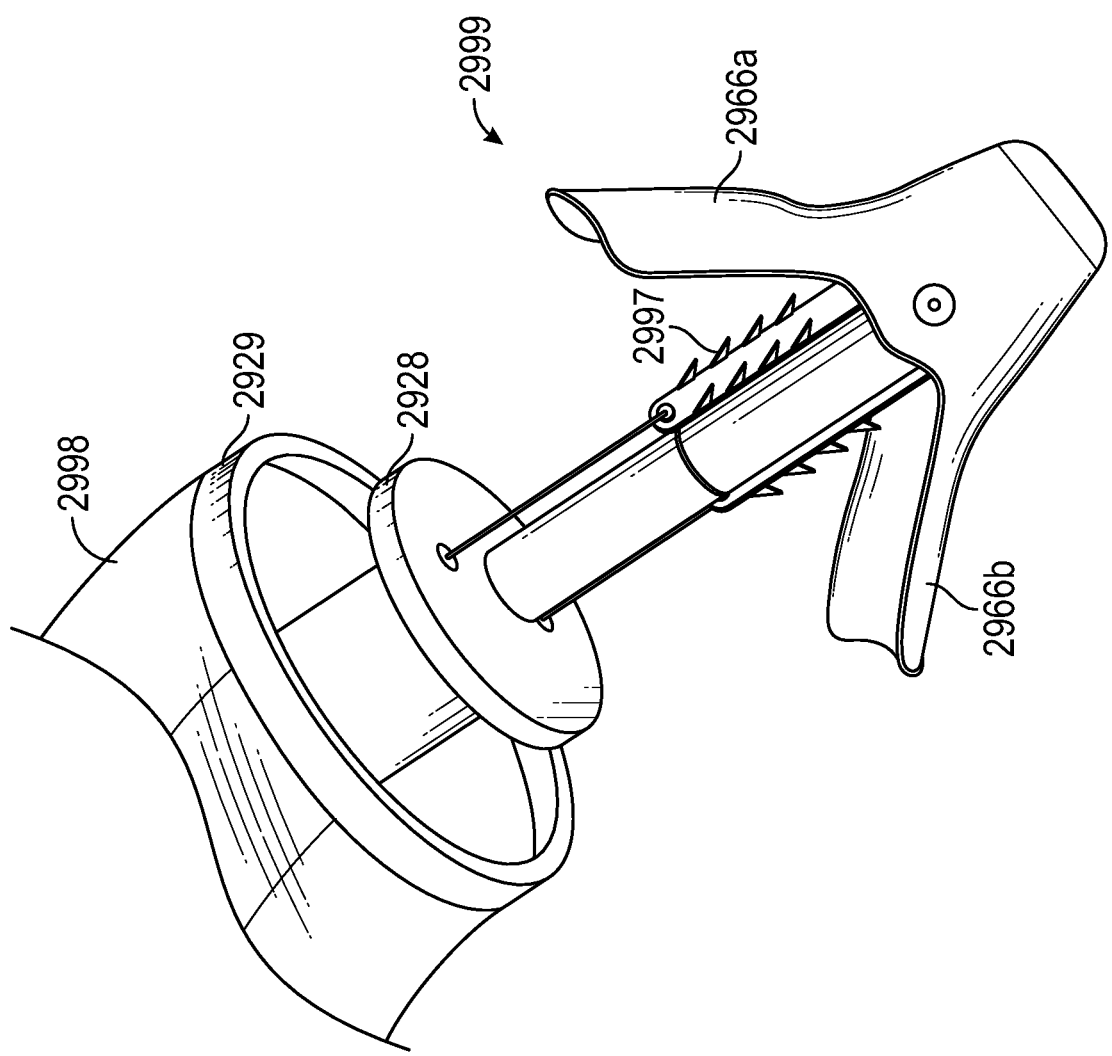
FIG. 29 shows an exemplary delivery device with magnetic elements.

In some embodiments, the stop and/or the cylindrical tip can be made of or include a magnet thereon, and the distal end of the elongate body can likewise be made of or include a magnet thereon. Thus, as shown in FIG. 29, an exemplary delivery system can include a magnet 2929 at the distal end of the elongate body 2998. For example, the magnet 2929 can be an annular magnetic ring forming the distal tip of the elongate body 2998. Further, the cylindrical tip can be made entirely (or partially) of a magnet 2928. The two magnets 2929, 2928 can be configured to repel each other when the stop or tip is near the distal end of the elongate body 2998. The magnetic force can be strong enough to provide tactile feedback to the physician as described above and yet weak enough to be overcome if desired (i.e., for movement of the cylindrical tip or stop into the distal end of the elongate catheter body 2998).

Advantageously, the single catheter steerable delivery system with a stop as described herein with respect to FIGS. 4A-16E and 29 can create the same curves in the same planes as a two catheter steerable delivery system. The delivery system described herein further advantageously provides a lower cost per procedure, fewer components, easier manufacturing, and easier use by the physician relative to a two catheter steerable delivery system. Moreover, the stop of the delivery systems descried herein advantageously prevents unwanted engagements of portions of the interventional device, such as a leaflet apposition device, with the inner diameter of the catheter. The single steerable catheter system described herein further allows for a larger diameter delivery catheter shaft, improving the torque transmission of the catheter.

Further, although the stops herein are primarily described as being used with a single catheter steerable system, they can also be used with a traditional two-catheter steerable system.

In some embodiments, a delivery system as described herein can include flexible retraction arms to assist in retracting the mitral valve leaflet apposition device. For example, referring to FIGS. 17A and 17B, an exemplary delivery system 1100 for a device, such as a mitral valve leaflet apposition device or clip 1111, is shown. As shown in FIG. 17A, the delivery system 1100 includes a guiding catheter or outer hollow elongate body 1101 and a catheter shaft 1107 extending therein. A coupling shaft 1117 extends from the catheter shaft 1107 for attachment to the apposition device 1111 through a coupling mechanism, such as a friction fit or locking element. Further, the inner diameter of the elongate body 1101 is sized such that the mitral valve leaflet apposition device 1111 can be attached to the coupling shaft 1117 (with the arms 1166a,b of the device 1111 closed to their low profile position) and then advanced through the elongate body 1101 from the proximal end of the elongate body 1101 to the distal end of the elongate body 1101 (e.g., by pushing on the catheter shaft 1107). The delivery system 1100 further includes a cylindrical tip 1103 positioned between the catheter shaft 1107 and coupling shaft 1117. Tether lines 1105a,b can extend therethrough for connection to barbed grippers of the device 1111.

The cylindrical tip 1103 includes flexible retraction arms 1122a,b attached thereto. As shown in FIG. 17A, the flexible retraction arms 1122a,b can be looped extensions configured to extend radially outwards from the tip 1103. When not constrained, the flexible retraction arms 1122a,b can extend, for example, substantially parallel to the plane of the tip 1103 and/or can extend partially proximally backwards towards the hollow elongate body 1101 (as shown in FIG. 17A). The flexible arms 1122a,b can further be rotationally oriented (i.e., positioned around the circumference pf the tip 1103) so that each flexible arm 1122a,b is aligned with a clip arm 1166a,b. The flexible arms 1122a,b can extend from the side of the cylindrical tip 1103 as shown or can be attached just proximal or distal of the tip 1103. Further, as shown in FIG. 17B, the flexible arms 1122a,b can be configured to flex to a low profile when inserted or retracted into the elongate body 1101 and to expand to a larger diameter when outside of the elongate body 1101, similar to the stops described above.

The flexible arms 1122a,b can each have a length in the collapsed configuration that is greater than the distance from the distal end of the cylindrical tip 1103 (or wherever the flexible arms 1122 are attached) to the proximal tips of the arms 1166a,b of the device 1111 in the closed configuration. Further, the length of each flexible arm 1122a,b in the collapsed configuration can be longer than the radial distance from the radial outer edge of the cylindrical tip 1103 (or wherever the flexible arm 1122a,b is attached) to the outer radial edge of the elongate body 1101. In the collapsed shape, the flexible arms 1122a,b can bend so that they can be withdrawn into an elongate body 1101 with an inner diameter of about 3 mm-8 mm, such as about 5.5 mm.

In use, the flexible arms 1122a,b can be used to help retract the clip 1111 back into the elongate body 1101. To retract the clip 1111, the clip arms 1166a,b can first be folded inwards around the coupling shaft 1117. As the elongate body 1101 is moved distally (and/or as the clip 1111 is pulled proximally), the elongate body 1101 can hit the flexible arms 1122a,b, causing them to fold or flex distally over the clip arms 1166a,b to pinch or hold them in place. The clip 1111 can then be fully covered by the elongate body 1101 and removed from the patient. The flexible arms 1122a,b can advantageously capture and pinch the arms 1166a,b and help center the clip 1111 during retraction, thereby helping to prevent the clip arms 1166a,b from getting caught on the edge of the elongate body 1101. Further, because the flexible arms 1122a,b can assist in pinching the clip arms 1166a,b more fully closed, the elongate body 1101 can have a smaller diameter (e.g., 0.006"-0.013" smaller) than an elongate body of a device that does not include flexible arms.

In some embodiments, the flexible arms 1122a,b in their unconstrained (i.e., expanded) configuration can extend in substantially the same plane as the cylindrical tip 1103. In such an embodiment, the flexible arms 1122a,b can together have a radial length ("wingspan") that is greater than the outer diameter of the elongate body. For example, the flexible arms 1122a,b can (when combined with the diameter of the stop 1103 connected thereto) have a radial length ("wingspan") of approximately 13-23 mm, such as 17-19 mm.

In other embodiments, the flexible arms 1122a,b in their unconstrained configuration can extend back towards the elongate body 1101 to form a 30-60 degree angle, such as a 45 degree angle, relative to the elongate body 1101. When angled, the flexible arms 1122a,b can have a diameter or radial length ("wingspan") of approximately 10-20 mm, such as 14-16 mm. By extending in the same plane as the cylindrical tip 1103 or proximally backwards, the flexible arms 1122a,b avoid interfering with the normal opening or closing of the clip arms 1166a,b. Further, by being angled at least slightly away from the elongate body 1101, the flexible arms 1122a,b can be more easily caught by the elongate body 1101 so as to aid in retraction of the device 1111 into the elongate body 1101.

Exemplary retraction of a clip 2111 with a device 2100 (having similar features to device 1100) is shown in FIGS. 18A-18D. As shown, as the elongate body 2101 is moved distally relative to the folded clip arms 2166a,b, the flexible arms 2122a,b can be pushed distally over the clip arms 2166a,b such that they further tighten the clip arms 2166a,b inwards to help guide the clip 2111 into the catheter 2101.

In many of the embodiments described herein, the flexible arms can be passively actuated (e.g., can self-expand automatically when the flexible arms are pushed out of the elongate body). In other embodiments, the flexible arms can be actively actuated. For example, as shown in in FIGS. 19A-19D, the device 6101 can include flexible arms 6122a,b that can be stored in a collapsed configuration within the delivery catheter shaft 6107 and/or the cylindrical tip 6103. Further, a control wire 6119 can extend within the delivery catheter shaft 6107 and can attach to the proximal end of the flexible arms 6122a,b. As the control wire 6119 is moved distally, it can push the flexible arms 6122a,b out of the delivery catheter shaft 6107 and/or the cylindrical tip 6103 (see the transition from FIGS. 19A/B to FIGS. 19C/D).

Figure 23A:
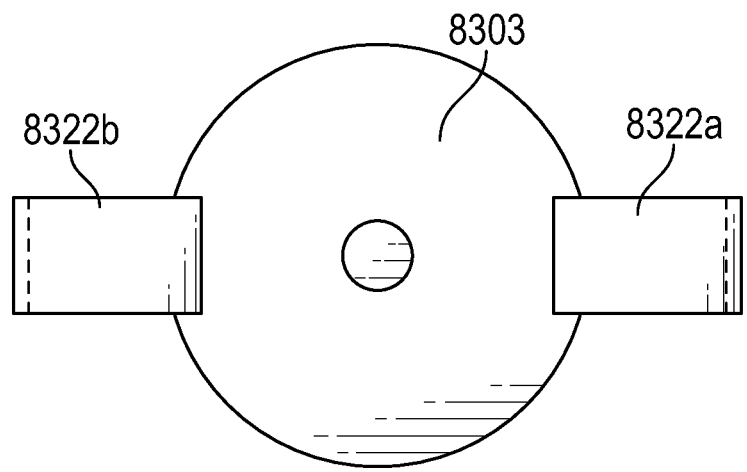
FIGS. 23A-23B show an exemplary embodiment of a delivery device with flexible annular arms.
Figure 23B:
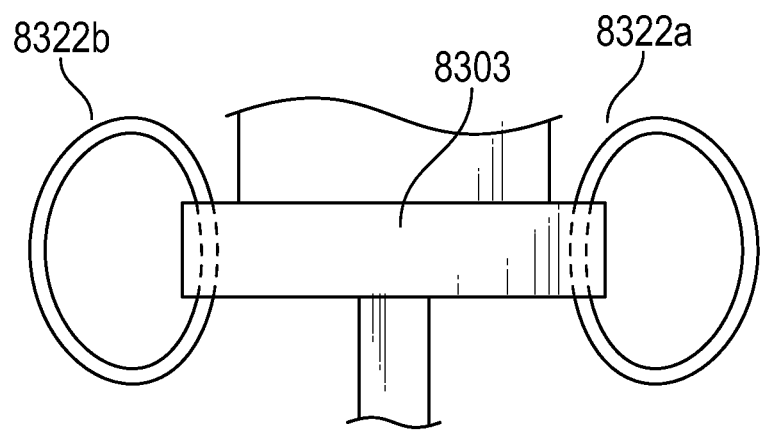
Figure 25A:
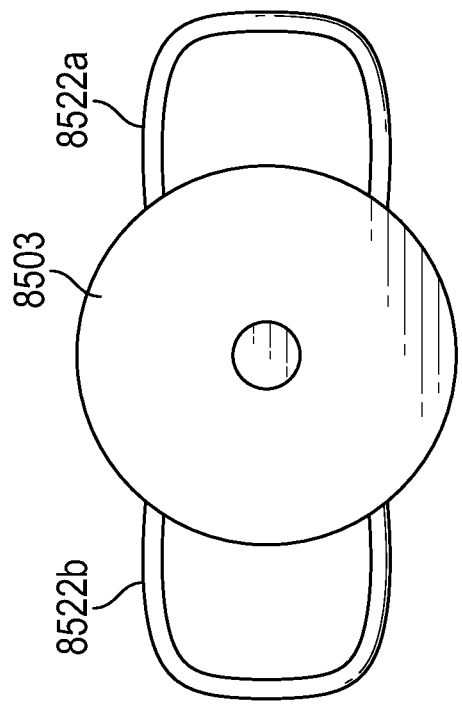
FIGS. 25A-25B show an exemplary embodiment of a delivery device with flexible arms.
Figure 25B:
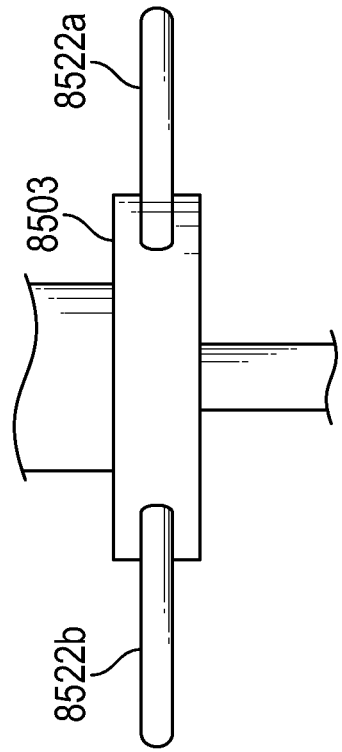
Figure 24A:
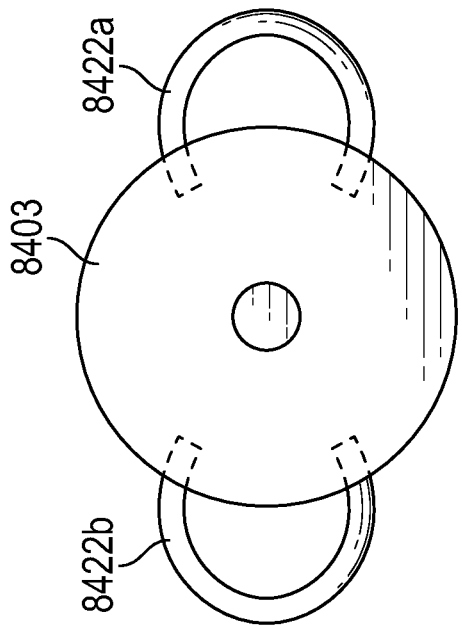
FIGS. 24A-24B show an exemplary embodiment of a delivery device with flexible arms.
Figure 24B:
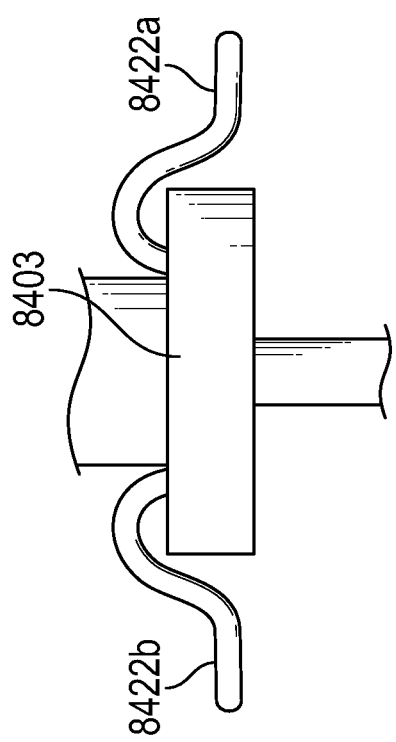
Figure 27A:
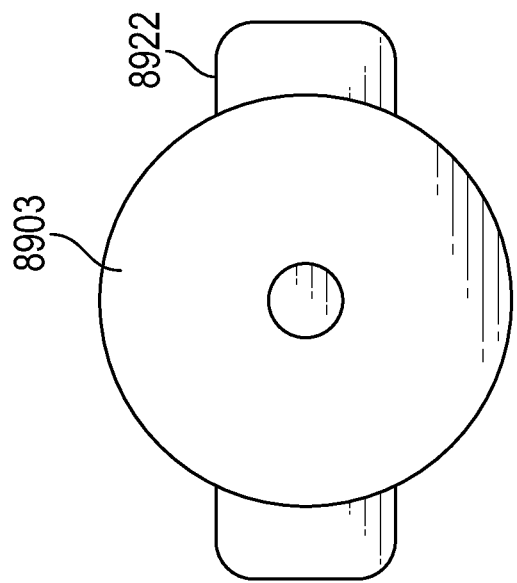
FIGS. 27A-27B show an exemplary embodiment of a delivery device with flexible arms.
Figure 27B:
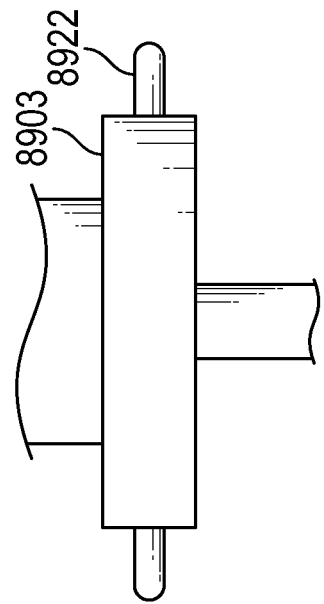
Figure 26A:
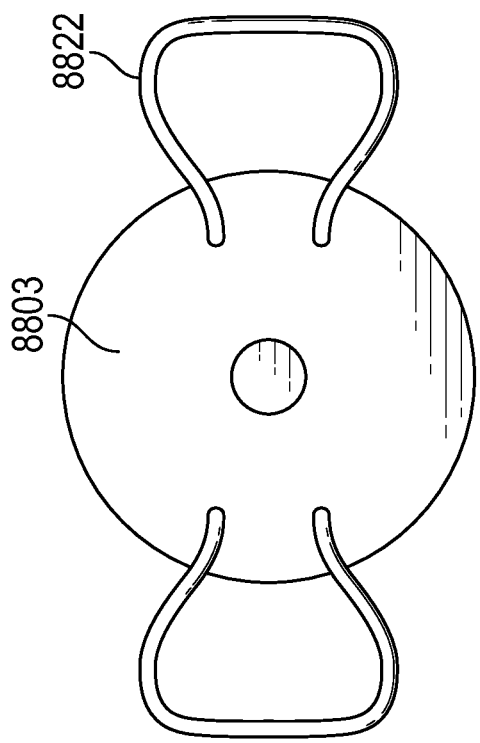
FIGS. 26A-26B show an exemplary embodiment of a delivery device with flexible arms.
Figure 26B:
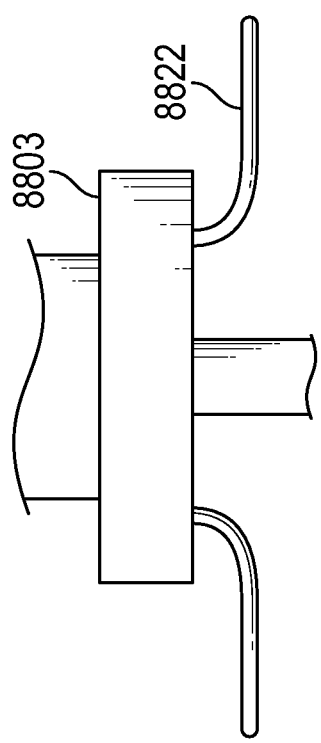

There can be 2, 3, 4 or more flexible arms in any of the delivery systems described herein. Further, the flexible arms described herein can take a variety of different shapes. For example, as shown in FIGS. 20A-20B, the flexible arms 7122a,b can be covered with a flexible mesh material, such as polyester or polytetrafluoroethylene (ePTFE). As shown in FIGS. 21A-21B, the flexible arms 8122a,b can each loop in a substantially oval shape. As shown in FIGS. 22A-22B, the flexible arms 9122a,b can each form a loop with undulations therein. As shown in FIGS. 23A and 23B, the flexible arms 8322a,b can be made of two or more flexible rings or cuff members attached to the tip 8303 such that the central axes of the cuffs are parallel to the plane of the tip 8303. As shown in FIGS. 24A and 24B, the flexible arms 8422a,b can each include a looped extension attached to the tip 8403. The looped extensions can, for example, be bent or flared along the central axis of the tip 8403, as shown in FIG. 24B. As shown in FIGS. 25A and 25B, the flexible arms 8522a,b can each include a looped extension extending straight out (radially) from the tip 8503. As shown in FIGS. 26A and 26B, the flexible arms 8822a,b can each include looped extensions that extend distally and then radially outwards relative to the tip 8803. As shown in FIGS. 27A and 27B, the flexible arms 8922a,b can each include tabs that extend radially outwards from the tip 8903.

The flexible arms described herein can be advantageous for use with a single steerable catheter system or with a double catheter steerable system. The flexible arms can also be used with a non-steerable catheter system.

In some embodiments, a delivery device can include combined features of the single catheter steerable delivery device with stop (described with respect to FIGS. 3A-16E) and the delivery device with retraction flexible arms (described with respect to FIGS. 17A-26B). That is, one or more extensions can function as both a stop (for a single steerable catheter delivery system) and a retraction aid (for either a single steerable catheter delivery system, or a system with two steerable catheters).

Figure 28B:
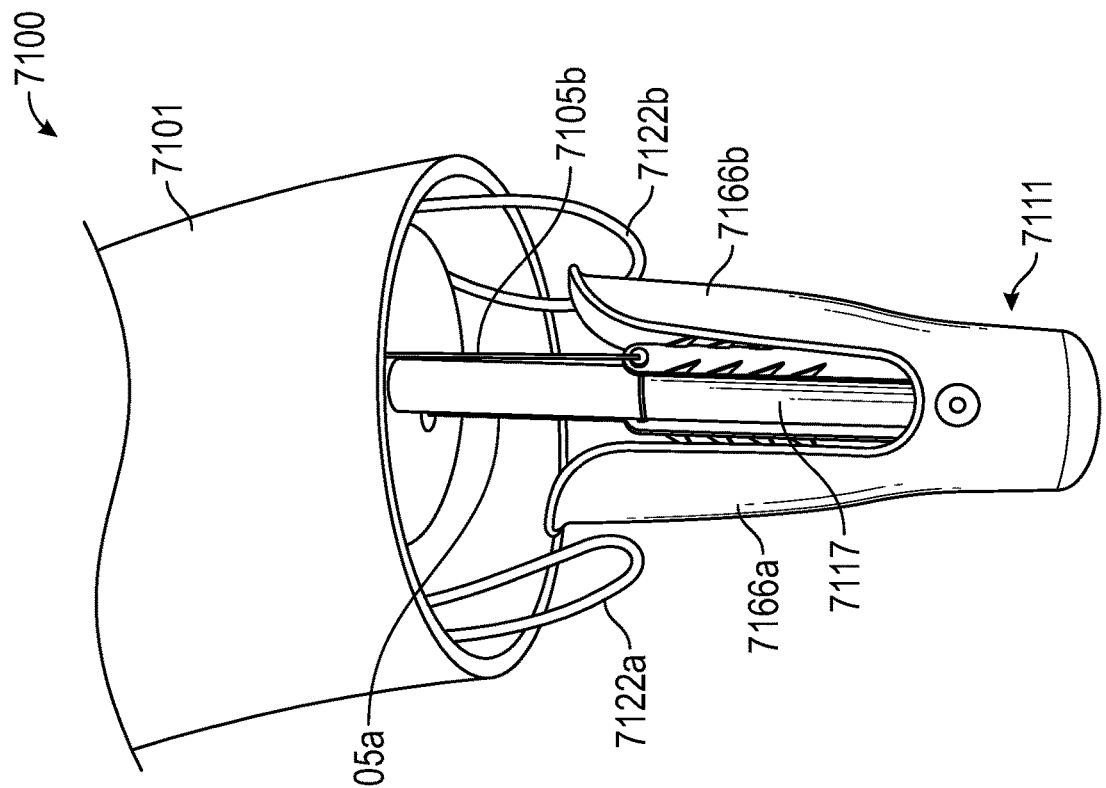
FIGS. 28A-28B show an exemplary delivery device with a combined stop/flexible arm retraction element.
Figure 28A:
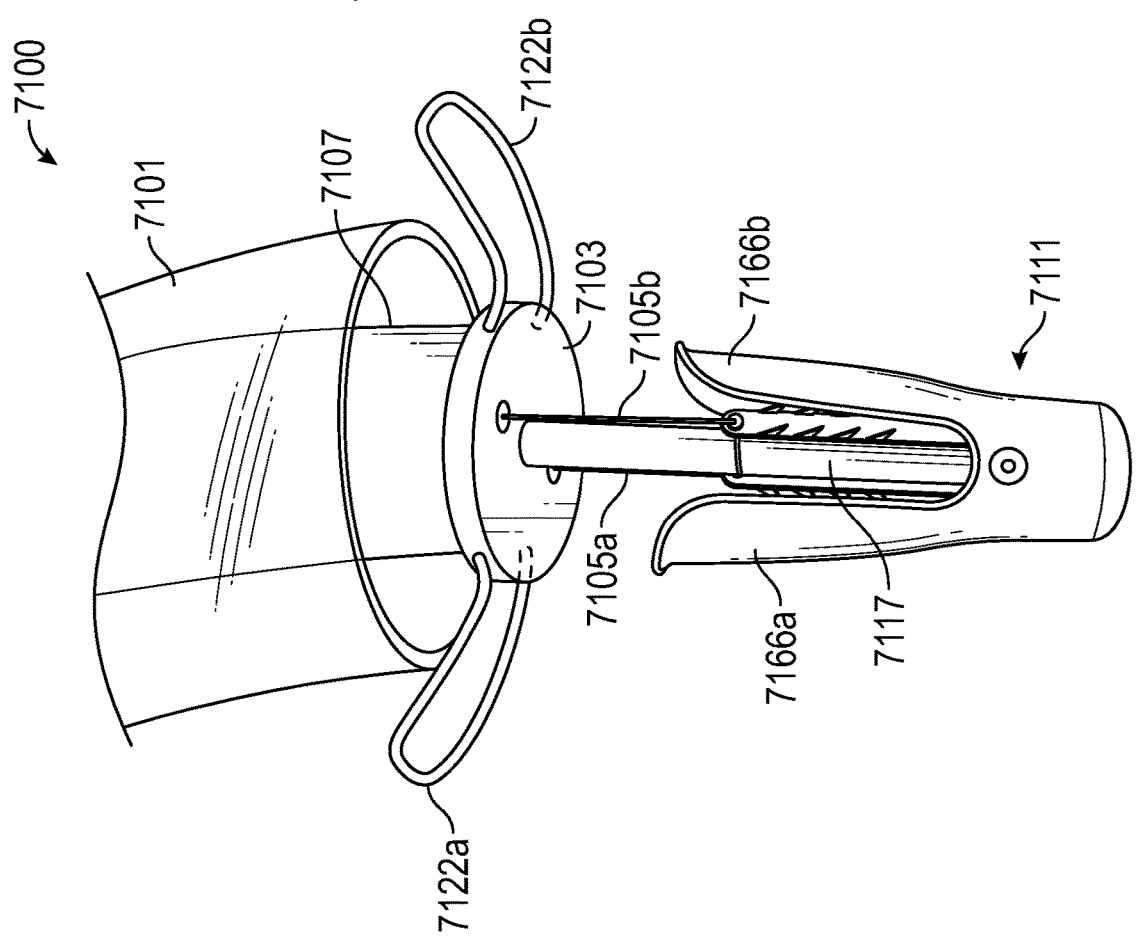

For example, FIGS. 28A-28B show single catheter steerable delivery system 7100 for a device, such as a mitral valve leaflet apposition device 7111. The delivery system 7100 includes an outer hollow elongate body 7101 and a catheter shaft 7107 extending therein. The outer elongate body 7101 can be steerable through use of a plurality of cables or tethers as described elsewhere herein. A coupling shaft 7117 extends from the catheter shaft 7107 for attachment to the apposition device 7111 through a coupling mechanism, such as a friction fit or locking element. The delivery system 1100 further includes a cylindrical tip 7103 positioned between the catheter shaft 7107 and coupling shaft 1117. Tether lines 7105a,b can extend therethrough for connection to the barbed grippers of the device 1111.

The cylindrical tip 7103 includes extensions 7122a,b attached thereto. As shown in FIG. 28A, the extensions 7122a,b can be configured to extend radially outwards from the tip 7103. When not constrained, the extensions 7122a,b can extend, for example, substantially parallel to the tip 7103 and/or can extend partially proximally backwards towards the hollow elongate body 7101 (as shown in FIG. 28A). The extensions 7122a,b can further be rotationally oriented (i.e., positioned around the circumference of the tip 7103) so that each extension 7122a,b is aligned with a clip arm 7166a,b. The extensions 7122a,b can extend from the side of the cylindrical tip 7103 and/or from the front or back of the tip 7103 (or can be attached just proximal or distal of the tip 7103). Further, as shown in FIG. 28B, the extensions 7122a,b are configured to flex to a low profile when inserted or retracted into the elongate body 7101 and to expand to a larger diameter when outside of the elongate body 7101. The extensions 7122a,b can have any of the characteristics or properties described herein with respect to the stops and/or the flexible retraction arms.

Advantageously, the extensions 7122a,b in their expanded configuration can provide tactile feedback to the physician when the flexible arms 7122a,b are pulled against the tip of the elongate body 7101, thereby both providing an indication that the device 7111 is fully extended outside of the elongate body (e.g., before releasing the arms 7166a,b) and also preventing the user from pulling the barbs 1112 proximally into the elongate body 7101 (which can catch on the inner diameter of the elongate body 101). When pulled proximally with additional force against the tip of the elongate body 7101, however, the arms 7122a,b can flex or change shape in order to extend over the folded clip arms 7166a,b to hold the clip arms 7166a,b down and aid in retracting the clip 7111 back into the elongate body 7101.

In any of the embodiments described herein, the stops and/or flexible retraction arms can be made of one or more flexible elements that are made of round wire or flat wire ("ribbon"). The flexible elements can be made of polymer or metal, such as nitinol or other shape memory alloy. In some embodiments, the wire can have a 0.005"-0.020" diameter, such as a 0.010" diameter. In some embodiments, the wire can change diameter along the length thereof. For example, the distal part of the wire loop can be tapered to have a smaller diameter so that it is more flexible in that region and/or the area near the cylindrical tip can be thinner to provide more flexibility for bending.

Any of the stops described herein can also be used as flexible arms for retraction. Similarly, any of the flexible arms described herein can be used as stops. To work as a combined stop and retraction aid, the arms (or stops) described herein can collapse to approximately 3-8 mm, preferably approximately 5.5 mm. Further, the length of the arms/stop (total wingspan) can be long enough to engage the clip arms as described above with respect to the flexible retraction arms.

In some embodiments, rather than flexing or bending to collapse, the flexible retraction arms and/or stops described herein can pivot about a pivot point to collapse.

The delivery systems described herein can be used with a variety of different devices and/or can be combined with features of other delivery device systems, as described in U.S. Pat. Nos. 8,216,256, 7,736,388; 7,682,369; 7,666,204; 7,655,015; 7,608,091; 7,604,646; 7,563,267; 7,464,712; 7,288,097; 7,226,467; 7,048,754; 6,770,083; 6,752,813; 6,629,534; 6,461,366; 6,269,819; each of which is incorporated by reference in its entirety. Although described herein as being used to deliver a mitral valve leaflet apposition device (for example, a mitral clip such as the MitraClip® device), the delivery systems described herein can be used to deliver a number of interventional devices, including an annulus-modification device, a chordal shortening device, or a regurgitation blocking device.

It should be understood that any feature described herein with respect to one embodiment can be combined with or substituted for any feature described herein with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the FIGS. is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A delivery system for an interventional device comprising:
    an elongate catheter body;
    a catheter shaft extending within the catheter body and configured to releasably attach to the interventional device; and
    at least one flexible element attached to a distal portion of the catheter shaft, the at least one flexible element having an expanded configuration in which the at least one flexible element extends beyond an outer circumference of the elongate catheter body and a collapsed configuration in which the at least one flexible element collapses within an inner circumference of the elongate catheter body;
    wherein the at least one flexible element in the expanded configuration is configured to provide a tactile stop when moved proximally relative to and against a distal end of the elongate catheter body with a first amount of force, and wherein the at least one flexible element is configured to collapse from the expanded configuration to the collapsed configuration to fit within the elongate catheter body when the at least one flexible element is moved relative to and against the distal end of the elongate catheter body with a second amount of force that is greater than the first amount of force, and
    wherein the at least one flexible element when moving proximally into the elongate catheter body and thereby collapsing from the expanded configuration to the collapsed configuration is configured to change shape to extend over the proximal end of the interventional device when the interventional device is attached to the catheter shaft.

2. The delivery system of claim 1, wherein the at least one flexible element is configured to self-expand from the collapsed configuration to the expanded configuration when released from the elongate catheter body.

3. The delivery system of claim 1, wherein the at least one flexible element includes two flexible elements, the two flexible elements positioned opposite one another about the distal portion of the catheter shaft.

4. The delivery system of claim 1, wherein the at least one flexible element is a looped element extending from the distal portion of the catheter shaft.

5. The delivery system of claim 1, wherein the at least one flexible element is a tab extending from the distal portion of the catheter shaft.

6. The delivery system of claim 1, wherein the at least one flexible element is at least a portion of an annular ring extending around the distal portion of the catheter shaft.

7. The delivery system of claim 1, wherein the at least one flexible element comprises a polymer.

8. The delivery system of claim 1, wherein the at least one flexible element comprises a shape memory alloy.

9. The delivery system of claim 1, wherein the at least one flexible element comprises stainless steel.

10. The delivery system of claim 1, wherein the elongate catheter body is steerable, and wherein the elongate catheter body is the only steerable elongate catheter body in the delivery system.

11. The delivery system of claim 1, wherein the at least one flexible element is attached to the distal portion of the catheter shaft at an attachment location, further wherein the at least one flexible member in the collapsed configuration has a length that is greater than a distance from the attachment location to the proximal end of the interventional device when the interventional device is attached to the catheter shaft.

12. The delivery system of claim 1, wherein the at least one flexible element is configured to extend substantially parallel to a plane of a tip of the elongate catheter body and/or to extend partially proximally backwards from the plane towards the elongate catheter body when the least one flexible element is in the expanded configuration.

13. The delivery system of claim 1, wherein the at least one flexible element is configured to recapture the proximal end of the interventional device when the interventional device is attached to the catheter shaft and the at least one flexible element is moved relative to and against the distal end of the elongate catheter body with the second amount of force.

14. A delivery system for an interventional device comprising:
    an elongate catheter body;
    a catheter shaft extending within the catheter body and configured to releasably attach to the interventional device; and
    at least one flexible element attached to a distal portion of the catheter shaft, the at least one flexible element having an expanded configuration in which the at least one flexible element extends beyond an outer circumference of the elongate catheter body and a collapsed configuration in which the at least one flexible element collapses within an inner circumference of the elongate catheter body,
    wherein the at least one flexible element in the expanded configuration is configured to provide a tactile stop when moved proximally relative to and against a distal end of the elongate catheter body with a first amount of force, and wherein the at least one flexible element is configured to collapse from the expanded configuration to the collapsed configuration to fit within the elongate catheter body when the at least one flexible element is moved relative to and against the distal end of the elongate catheter body with a second amount of force that is greater than the first amount of force, and
    wherein the at least one flexible element is configured to recapture the proximal end of the interventional device when the at least one flexible element is moved relative to and against the distal end of the elongate catheter body with the second amount of force when the interventional device is attached to the catheter shaft.

15. The delivery system of claim 14, wherein the at least one flexible element is configured to extend substantially parallel to a plane of a tip of the elongate catheter body and/or to extend partially proximally backwards from the plane towards the elongate catheter body when the at least one flexible element is in the expanded configuration.

16. A delivery system for an interventional device comprising:
    an elongate catheter body;
    a catheter shaft extending within the catheter body and configured to releasably attach to the interventional device; and
    at least one flexible element attached to a distal portion of the catheter shaft, the at least one flexible element having an expanded configuration in which the at least one flexible element extends beyond an outer circumference of the elongate catheter body and a collapsed configuration in which the at least one flexible element collapses within an inner circumference of the elongate catheter body,
    wherein the at least one flexible element in the expanded configuration is configured to provide a tactile stop when moved proximally relative to and against a distal end of the elongate catheter body with a first amount of force, and wherein the at least one flexible element is configured to collapse from the expanded configuration to the collapsed configuration to fit within the elongate catheter body when the at least one flexible element is moved relative to and against the distal end of the elongate catheter body with a second amount of force that is greater than the first amount of force, and
    wherein the at least one flexible element is configured to extend substantially parallel to a plane of a tip of the elongate catheter body and/or to extend partially proximally backwards from the plane towards the elongate catheter body when the at least one flexible element is in the expanded configuration.

* * * * *